US011382855B2

(12) United States Patent
Bernard et al.

(10) Patent No.: US 11,382,855 B2
(45) Date of Patent: *Jul. 12, 2022

(54) COMPOSITIONS AND METHODS FOR IMPROVING THE APPEARANCE OF THE SKIN

(71) Applicant: L'OREAL, Paris (FR)

(72) Inventors: Anne-Laure Suzanne Bernard, New York, NY (US); Yang Deng, Edison, NJ (US); Hy Si Bui, Piscataway, NJ (US); Laure Daubersies, Paris (FR); Roshanak Debeaud, L'hay les Roses (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/537,099

(22) PCT Filed: Dec. 17, 2015

(86) PCT No.: PCT/US2015/066420
§ 371 (c)(1),
(2) Date: Jan. 5, 2018

(87) PCT Pub. No.: WO2016/100690
PCT Pub. Date: Jun. 23, 2016

(65) Prior Publication Data
US 2018/0015023 A1 Jan. 18, 2018

Related U.S. Application Data

(60) Provisional application No. 62/093,946, filed on Dec. 18, 2014.

(30) Foreign Application Priority Data

| Dec. 18, 2014 | (FR) | 1462721 |
| Dec. 18, 2014 | (FR) | 1462725 |
| Dec. 18, 2014 | (FR) | 1462731 |
| Dec. 18, 2014 | (FR) | 1462829 |

(51) Int. Cl.
| A61K 8/898 | (2006.01) |
| A61K 8/25 | (2006.01) |
| A61Q 19/08 | (2006.01) |
| A61K 8/891 | (2006.01) |
| A61K 8/81 | (2006.01) |
| A61K 8/90 | (2006.01) |
| A61K 8/02 | (2006.01) |
| A61K 8/31 | (2006.01) |
| A61K 8/58 | (2006.01) |
| A61Q 19/00 | (2006.01) |
| A61K 8/19 | (2006.01) |
| A61K 8/29 | (2006.01) |
| A61K 8/88 | (2006.01) |
| A61Q 19/02 | (2006.01) |
| A61Q 17/04 | (2006.01) |

(52) U.S. Cl.
CPC ............ *A61K 8/898* (2013.01); *A61K 8/02* (2013.01); *A61K 8/19* (2013.01); *A61K 8/25* (2013.01); *A61K 8/29* (2013.01); *A61K 8/31* (2013.01); *A61K 8/585* (2013.01); *A61K 8/8117* (2013.01); *A61K 8/8152* (2013.01); *A61K 8/8194* (2013.01); *A61K 8/88* (2013.01); *A61K 8/891* (2013.01); *A61K 8/90* (2013.01); *A61Q 17/04* (2013.01); *A61Q 19/00* (2013.01); *A61Q 19/02* (2013.01); *A61Q 19/08* (2013.01); *A61K 2800/262* (2013.01); *A61K 2800/43* (2013.01)

(58) Field of Classification Search
CPC ........ A61Q 19/00; A61K 8/8152; A61K 8/90; A61K 8/25; A61K 8/585; A61K 8/31; A61K 8/8194; A61K 8/19; A61K 2800/594; A61K 8/8111; A61K 8/26; A61K 8/8147; A61K 8/0241

See application file for complete search history.

(56) References Cited

U.S. PATENT DOCUMENTS

| 2,463,264 A | 3/1949 | Graenacher et al. |
| 3,635,743 A | 1/1972 | Smith |
| 3,957,713 A | 5/1976 | Jeram et al. |
| 4,693,935 A | 9/1987 | Mazurek |
| 4,725,658 A | 2/1988 | Thayer et al. |
| 4,972,037 A | 11/1990 | Garbe et al. |
| 4,981,902 A | 1/1991 | Mitra et al. |

(Continued)

FOREIGN PATENT DOCUMENTS

| CN | 1249170 A | 4/2000 |
| CN | 1397265 A | 2/2003 |

(Continued)

OTHER PUBLICATIONS

JP 56020515 A, English Derwent abstract, downloaded 2019 (Year: 2019).*

(Continued)

*Primary Examiner* — Mark V Stevens
(74) *Attorney, Agent, or Firm* — The Marbury Law Group, PLLC

(57) ABSTRACT

The disclosure relates to compositions and methods for improving the appearance of the skin. Compositions comprise at least one thermoplastic elastomer, at least one adhesive polymer, and at least one filler. Methods comprise applying the compositions to the skin to tighten the skin or hide skin imperfections by forming a film on the skin.

22 Claims, No Drawings

(56) References Cited

U.S. PATENT DOCUMENTS

| | | | |
|---|---|---|---|
| 4,981,903 A | 1/1991 | Garbe et al. |
| 5,011,681 A | 4/1991 | Ciotti et al. |
| 5,061,481 A | 10/1991 | Suzuki et al. |
| 5,166,355 A | 11/1992 | Leistner et al. |
| 5,209,924 A | 5/1993 | Garbe et al. |
| 5,219,560 A | 6/1993 | Suzuki et al. |
| 5,236,986 A | 8/1993 | Sakuta |
| 5,237,071 A | 8/1993 | Leistner et al. |
| 5,262,087 A | 11/1993 | Tachibana et al. |
| 5,334,737 A | 8/1994 | Thimineur et al. |
| 5,380,455 A | 1/1995 | Tsuda et al. |
| 5,412,004 A | 5/1995 | Tachibana et al. |
| 5,468,477 A | 11/1995 | Kumar et al. |
| 5,585,091 A | 12/1996 | Pelzer et al. |
| 5,624,663 A | 4/1997 | Deflandre et al. |
| 5,645,609 A | 7/1997 | Andrean et al. |
| 5,665,687 A | 9/1997 | Khayat et al. |
| 5,691,172 A | 11/1997 | Belcour et al. |
| 5,711,940 A | 1/1998 | Kuentz et al. |
| 5,811,487 A | 9/1998 | Schulz, Jr |
| 5,837,793 A | 11/1998 | Harashima et al. |
| 5,851,517 A * | 12/1998 | Mougin ............ A61K 8/044 424/78.02 |
| 5,879,688 A | 3/1999 | Coury et al. |
| 5,972,329 A | 10/1999 | Chuang et al. |
| 5,977,280 A | 11/1999 | Kadlec et al. |
| 6,045,782 A | 4/2000 | Krog et al. |
| 6,051,216 A | 4/2000 | Barr et al. |
| 6,080,415 A | 6/2000 | Simon |
| 6,093,385 A | 7/2000 | Habeck et al. |
| 6,159,455 A | 12/2000 | Habeck et al. |
| 6,191,301 B1 | 2/2001 | Habeck et al. |
| 6,225,467 B1 | 5/2001 | Esteghamatian et al. |
| 6,238,649 B1 | 5/2001 | Habeck et al. |
| 6,261,544 B1 | 7/2001 | Coury et al. |
| 6,284,233 B1 | 9/2001 | Simon et al. |
| 6,338,839 B1 | 1/2002 | Auguste et al. |
| 6,338,855 B1 | 1/2002 | Albacarys et al. |
| 6,342,469 B1 | 1/2002 | Lorant |
| 6,353,076 B1 | 3/2002 | Barr et al. |
| 6,387,355 B2 | 5/2002 | Heidenfelder et al. |
| 6,391,289 B2 | 5/2002 | Heidenfelder et al. |
| 6,423,306 B2 | 7/2002 | Caes et al. |
| 6,436,373 B1 | 8/2002 | Habeck et al. |
| 6,451,295 B1 | 9/2002 | Cai et al. |
| 7,306,771 B2 | 12/2007 | Okawara |
| 7,311,897 B2 | 12/2007 | Ehlis et al. |
| 7,374,771 B2 | 5/2008 | Eversheim et al. |
| 7,470,725 B2 | 12/2008 | Schwertfeger et al. |
| 7,582,719 B1 | 9/2009 | Tan et al. |
| 7,700,084 B2 | 4/2010 | Delage-Grouiller et al. |
| 7,758,848 B2 | 7/2010 | Lu et al. |
| 7,803,877 B2 | 9/2010 | Lion et al. |
| 7,879,316 B2 | 2/2011 | Ferrari et al. |
| 7,993,661 B2 | 8/2011 | Arnaud et al. |
| 8,673,283 B2 | 3/2014 | Bui et al. |
| 8,691,202 B2 | 4/2014 | Yu et al. |
| 9,895,561 B2 | 2/2018 | Ilekti et al. |
| 10,335,361 B2 | 7/2019 | Cavazzuti et al. |
| 10,864,157 B2 | 12/2020 | Bernard et al. |
| 2002/0001570 A1 | 1/2002 | Heidenfelder et al. |
| 2002/0004034 A1 | 1/2002 | Heidenfelder et al. |
| 2002/0016310 A1 | 2/2002 | Habeck et al. |
| 2003/0017124 A1 | 1/2003 | Agostini et al. |
| 2003/0026815 A1 | 2/2003 | Scott et al. |
| 2003/0059392 A1 | 3/2003 | L'Alloret |
| 2003/0068344 A1 | 4/2003 | Ferrari et al. |
| 2003/0091520 A1 | 5/2003 | Livoreil et al. |
| 2003/0157047 A1 | 8/2003 | Lennon et al. |
| 2003/0158363 A1 | 8/2003 | Nakanishi |
| 2004/0013624 A1 | 1/2004 | Mateu et al. |
| 2004/0137028 A1 | 7/2004 | De La Poterie |
| 2004/0191191 A1 | 9/2004 | Ehlis et al. |
| 2004/0192832 A1 | 9/2004 | Cordier |
| 2004/0197284 A1 | 10/2004 | Auguste |
| 2004/0213747 A1 | 10/2004 | Patil et al. |
| 2005/0008667 A1 | 1/2005 | Liechty et al. |
| 2005/0013782 A1 | 1/2005 | Goppel et al. |
| 2005/0069564 A1 | 3/2005 | Eversheim et al. |
| 2005/0183511 A1 | 8/2005 | Giron |
| 2005/0186166 A1 | 8/2005 | Patil et al. |
| 2005/0239950 A1 | 10/2005 | Martin et al. |
| 2005/0244974 A1 | 11/2005 | Garcia-Franco et al. |
| 2005/0287088 A1 | 12/2005 | Guiramand et al. |
| 2006/0034875 A1 | 2/2006 | Nakanishi et al. |
| 2006/0193801 A1 | 8/2006 | Blin et al. |
| 2006/0193803 A1 | 8/2006 | Farcet |
| 2007/0041928 A1 | 2/2007 | Chen et al. |
| 2007/0055014 A1 | 3/2007 | Lu et al. |
| 2007/0140991 A1 | 6/2007 | Maitra et al. |
| 2007/0224147 A1 | 9/2007 | Richard |
| 2007/0258923 A1 | 11/2007 | Bui et al. |
| 2007/0258924 A1 | 11/2007 | Bui et al. |
| 2007/0258934 A1 | 11/2007 | Bui et al. |
| 2008/0102048 A1 | 5/2008 | McDermott |
| 2008/0102049 A1* | 5/2008 | McDermott ............ A61K 8/26 424/64 |
| 2008/0107615 A1* | 5/2008 | Keene ............ A61K 8/044 424/70.7 |
| 2008/0233075 A1 | 9/2008 | Sokolinsky et al. |
| 2009/0074689 A1 | 3/2009 | Auguste |
| 2010/0009931 A1 | 1/2010 | Laboreau et al. |
| 2010/0197805 A1 | 8/2010 | Cassin |
| 2011/0020263 A1 | 1/2011 | Ilekti et al. |
| 2011/0098424 A1 | 4/2011 | Carpentier et al. |
| 2011/0123650 A1 | 5/2011 | Kimura |
| 2011/0243864 A1 | 10/2011 | Farcet et al. |
| 2013/0028851 A1* | 1/2013 | Fontaine ............ A61K 8/27 424/59 |
| 2013/0078209 A1 | 3/2013 | Yu et al. |
| 2013/0164235 A1 | 6/2013 | Lebre-Lemonnier et al. |
| 2013/0202546 A1 | 8/2013 | Howell |
| 2013/0236406 A1* | 9/2013 | Tong ............ A61Q 1/04 424/64 |
| 2013/0236407 A1 | 9/2013 | Tong et al. |
| 2013/0236408 A1 | 9/2013 | Bui et al. |
| 2013/0236409 A1 | 9/2013 | Bui et al. |
| 2014/0004073 A1 | 1/2014 | Yu et al. |
| 2015/0272853 A1 | 10/2015 | Kishina et al. |
| 2015/0366789 A1 | 12/2015 | Mei et al. |
| 2016/0000670 A1 | 1/2016 | Pesaro et al. |
| 2017/0189321 A1 | 7/2017 | Bernard et al. |
| 2018/0015023 A1 | 1/2018 | Bernard et al. |
| 2019/0091130 A1 | 3/2019 | Farran et al. |
| 2019/0091134 A1 | 3/2019 | Bernard et al. |

FOREIGN PATENT DOCUMENTS

| | | |
|---|---|---|
| CN | 1415280 A | 5/2003 |
| CN | 1490500 A | 4/2004 |
| CN | 1504488 A | 6/2004 |
| CN | 1572287 A | 2/2005 |
| CN | 101084864 A | 12/2007 |
| CN | 101843569 A | 9/2010 |
| CN | 103037836 A | 4/2013 |
| CN | 103153279 A | 6/2013 |
| DE | 19726184 A1 | 12/1998 |
| DE | 19746654 A1 | 2/1999 |
| DE | 19755649 A1 | 6/1999 |
| DE | 19855649 A1 | 6/2000 |
| DE | 10162844 A1 | 7/2003 |
| EP | 0669323 A1 | 8/1995 |
| EP | 0749747 A1 | 12/1996 |
| EP | 0832642 A2 | 4/1998 |
| EP | 0893119 A1 | 1/1999 |
| EP | 0967200 A1 | 12/1999 |
| EP | 1008586 A1 | 6/2000 |
| EP | 1027883 A2 | 8/2000 |
| EP | 1133980 A2 | 9/2001 |
| EP | 1133981 A2 | 9/2001 |
| EP | 1300137 A2 | 4/2003 |
| FR | 2679771 A1 | 2/1993 |
| FR | 2785530 A1 | 5/2000 |

(56) References Cited

FOREIGN PATENT DOCUMENTS

| | | | |
|---|---|---|---|
| FR | 2860155 | A1 | 4/2005 |
| FR | 2863493 | A1 | 6/2005 |
| FR | 2887446 | A1 | 12/2006 |
| FR | 2951641 | A1 | 4/2011 |
| FR | 2983717 | A1 | 6/2013 |
| GB | 2303549 | A | 2/1997 |
| JP | 56020515 | A * | 2/1981 |
| JP | H2-223508 | A | 9/1990 |
| JP | H11-502228 | A | 2/1999 |
| JP | 2000-086491 | A | 3/2000 |
| JP | 2002-302421 | A | 10/2002 |
| JP | 2002-537314 | A | 11/2002 |
| JP | 2004-277299 | A | 10/2004 |
| JP | 2006-143714 | A | 6/2006 |
| JP | 2006-213717 | A | 8/2006 |
| JP | 2007-023037 | A | 2/2007 |
| JP | 2007-506708 | A | 3/2007 |
| JP | 2007-203491 | A | 8/2007 |
| JP | 2007-297391 | A | 11/2007 |
| JP | 2009-536185 | A | 10/2009 |
| JP | 2014-172909 | A | 9/2014 |
| KR | 10-2010-0129713 | A | 12/2010 |
| WO | 93/04665 | A1 | 3/1993 |
| WO | 01/32737 | A1 | 5/2001 |
| WO | 03/042221 | A1 | 5/2003 |
| WO | 2004/006878 | A1 | 1/2004 |
| WO | 2004/024798 | A1 | 3/2004 |
| WO | 2004/085412 | A1 | 10/2004 |
| WO | 2005/030155 | A1 | 4/2005 |
| WO | 2005/030158 | A1 | 4/2005 |
| WO | 2005/058269 | A1 | 6/2005 |
| WO | 2005/100444 | A1 | 10/2005 |
| WO | 2006/032741 | A1 | 3/2006 |
| WO | 2006/034982 | A1 | 4/2006 |
| WO | 2006/034985 | A1 | 4/2006 |
| WO | 2006/034991 | A1 | 4/2006 |
| WO | 2006/034992 | A1 | 4/2006 |
| WO | 2006/035000 | A1 | 4/2006 |
| WO | 2006/035007 | A1 | 4/2006 |
| WO | 2008/075283 | A2 | 6/2008 |
| WO | 2012/030984 | A2 | 3/2012 |
| WO | 2013/190136 | A1 | 12/2013 |
| WO | 2013/190709 | A1 | 12/2013 |
| WO | 2014/143757 | A1 | 9/2014 |
| WO | 2014/167543 | A1 | 10/2014 |
| WO | 2015/091513 | A1 | 6/2015 |
| WO | 2016/100742 | A1 | 6/2016 |
| WO | 2016/100743 | A1 | 6/2016 |
| WO | 2016/100746 | A1 | 6/2016 |
| WO | 2017/117420 | A1 | 7/2017 |
| WO | 2017/117426 | A1 | 7/2017 |
| WO | 2017/117438 | A1 | 7/2017 |

OTHER PUBLICATIONS

JP-56020515-A, Derwent Abstract in English, 1981 (Year: 1981).*
Armstrong and Bird (Cosmetics design.com USA, 2009, https://www.cosmeticsdesign.com/Article/2009/05/26/Dow-Corning-silicone-blends-work-with-wider-ingredients-range) (Year: 2009).*
Non-Final Office Action for co-pending U.S. Appl. No. 15/094,259, dated Mar. 8, 2019.
Co-Pending U.S. Appl. No. 16/367,568, entitled "Compositions for Removing Cosmetic Films," Inventors: Anne-Laure Suzanne Bernard et al., filed Mar. 28, 2019.
Non-Final Office Action for copending U.S. Appl. No. 15/396,862, dated Oct. 1, 2018.
Final Office Action for copending U.S. Appl. No. 15/087,066, dated Oct. 25, 2018.
Extended European Search Report for counterpart Application No. 15871123.4-1114, dated Sep. 12, 2018.
Notice of Allowance for copending U.S. Appl. No. 15/087,115, dated Feb. 1, 2019.
Non-Final Office Action for copending U.S. Appl. No. 15/087,115, dated Jul. 27, 2018.
International Preliminary Report on Patentability for counterpart Application No. PCT/US2016/069271, dated Jul. 12, 2018.
International Preliminary Report on Patentability for counterpart Application No. PCT/US2016/069278, dated Jul. 12, 2018.
International Preliminary Report on Patentability for counterpart Application No. PCT/US2016/069294, dated Jul. 12, 2018.
Non-Final Office Action for copending U.S. Appl. No. 15/087,066, dated May 9, 2018.
Final Office Action for copending U.S. Appl. No. 15/087,115, dated Jan. 26, 2018.
Final Office Action for copending U.S. Appl. No. 15/094,259, dated Jan. 25, 2018.
Final Office Action for copending U.S. Appl. No. 15/087,066, dated Jan. 22, 2018.
Burnett, Draft Report on Nylon, Cosmetic Ingredient Review, Jun. 11, 2012, pp. 1-40.
Mallard Creek Polymers, "Understanding the Glass Transition Temperature," Nov. 10, 2015 [retrieved from http://www.mcpolymers.com/library/understanding-the-glasstransition-temperature, Feb. 12, 2017].
International Search Report and Written Opinion for PCT/US2015/066420, dated Feb. 26, 2016.
International Search Report and Written Opinion for PCT/US2015/066510, dated Feb. 26, 2016.
International Search Report and Written Opinion for PCT/US2015/066513, dated Feb. 26, 2016.
International Search Report and Written Opinion for PCT/US2015/066516, dated Mar. 3, 2016.
International Search Report and Written Opinion for PCT/US2016/069278, dated Mar. 13, 2017.
International Search Report and Written Opinion for PCT/US2016/069271, dated Mar. 16, 2017.
International Search Report and Written Opinion for PCT/US2016/069294, dated Mar. 24, 2017.
Non-Final Office Action for copending U.S. Appl. No. 15/094,259, dated Apr. 20, 2017.
International Preliminary Report on Patentability for PCT/US2015/066420, dated Jun. 29, 2017.
International Preliminary Report on Patentability for PCT/US2015/066516, dated Jun. 29, 2017.
International Preliminary Report on Patentability for PCT/US2015/066510, dated Jun. 29, 2017.
International Preliminary Report on Patentability for PCT/US2015/066513, dated Jun. 29, 2017.
Non-Final Office Action for co-pending U.S. Appl. No. 15/087,115, dated Jul. 20, 2017.
Non-Final Office Action for co-pending U.S. Appl. No. 15/087,066, dated Sep. 15, 2017.
Sigma-Aldrich specification sheet for poly(dimethylsiloxane-co-methylhydroslloxane) trimethylsilyl terminated (1 page, accessed Sep. 11, 2017, http://www.sigmaaldrich.com/catalog/product/aldrich/482196?lang=en&region=US).
Final Office Action for co-pending U.S. Appl. No. 15/537,122, dated Aug. 9, 2019.
Non-Final Office Action for co-pending U.S. Appl. No. 15/537,130, dated Aug. 20, 2019.
Gold et al., "Here's What You Need to Know About Titanium Dioxide and Zinc Oxide Sunscreens," Women's Health, Titanium Dioxide and Zinc Oxide—What is Mineral Sunscreen, accessed Aug. 13, 2019, pp. 1-10.
Final Office Action for co-pending U.S. Appl. No. 15/087,066, dated Oct. 21, 2019.
Non-Final Office Action for co-pending U.S. Appl. No. 15/537,122, dated May 17, 2019.
Final Office Action for co-pending U.S. Appl. No. 15/394,862, dated May 31, 2019.
Extended European Search Report for counterpart Application No. 16882678.2-1114, dated May 17, 2019.
Non-Final Office Action for co-pending U.S. Appl. No. 15/087,066, dated Jun. 20, 2019.
Brazilian Office Action for counterpart Application No. BR112017012836-5, dated Aug. 27, 2019, with Translation.

(56) References Cited

OTHER PUBLICATIONS

Brazilian Office Action for counterpart Application No. BR112017012667-2, dated Aug. 27, 2019, with Translation.
Brazilian Office Action for counterpart Application No. BR112017012663-0, dated Sep. 6, 2019, with Translation.
European Office Action for counterpart Application No. 15871083.0-1114, dated Aug. 20, 2019.
European Office Action for counterpart Application No. 15871124.2-1114, dated Aug. 20, 2019.
European Office Action for counterpart Application No. 15871123.4-1114, dated Aug. 12, 2019.
Brazilian Office Action for counterpart Application No. BR112017012615-0, dated Aug. 27, 2019, with Translation.
Final Office Action for co-pending U.S. Appl. No. 15/094,259, dated Sep. 19, 2019.
Bornholtz, "8 Foundation Hacks You Need to Know," Women's Health, available online Nov. 17, 2014.
Non-Final Office Action for co-pending U.S. Appl. No. 15/394,862, dated Oct. 3, 2019.
Translated Japanese First Office Action for counterpart Application No. 2017-532891, dated Dec. 2, 2019.
Translation of First Office Action for counterpart CN Application No. 201580076415X, dated Oct. 23, 2019.
Search Report for counterpart CN Application No. 201580076415X, dated Oct. 23, 2019.
Translation of First Office Action for counterpart CN Application No. 2015800761946, dated Oct. 24, 2019.
Search Report for counterpart CN Application No. 2015800761946, dated Oct. 24, 2019.
Translation of First Office Action for counterpart CN Application No. 2015800764427, dated Nov. 4, 2019.
Search Report for counterpart CN Application No. 2015800764427, dated Nov. 4, 2019.
Non-Final Office Action for counterpart Japanese Application No. 2017-532869, dated Jan. 6, 2020.
Non-Final Office Action for counterpart Japanese Application No. 2017-532876, dated Jan. 6, 2020.
Translation of Japanese Office Action for counterpart Application No. 2018-534805, dated Dec. 9, 2019.
Translation of Japanese Office Action for counterpart Application No. 2017-532875, dated Dec. 9, 2019.
Final Office Action for copending U.S. Appl. No. 15/394,862, dated Mar. 24, 2020.
Non-Final Office Action for copending U.S. Appl. No. 15/094,259, dated Apr. 3, 2020.
Final Office Action for co-pending U.S. Appl. No. 15/537,130, dated Feb. 7, 2020.
Non-Final Office Action for co-pending U.S. Appl. No. 15/537,122, dated Feb. 24, 2020.
Translated First Office Action for counterpart CN Application No. 201580076414.5, dated Jan. 10, 2020.
Search Report for counterpart CN Application No. 201580076414.5, dated Jan. 2, 2020.
Brazilian Office Action and translated Written Opinion for counterpart Application No. BR112018013350, dated Feb. 28, 2020.
Non-Final Office Action for copending U.S. Appl. No. 15/537,112, dated Jun. 2, 2020.
Non-Final Office Action for copending U.S. Appl. No. 16/367,568, dated Jul. 17, 2020.
European Office Action for counterpart Application No. 16 882 678.2-1112, dated Jul. 20, 2020.
Translated Chinese Office Action for counterpart Application No. 201580076442-7, dated Jul. 30, 2020.
Translated Japanese Office Action for counterpart Application No. 2017-532875, dated Aug. 3, 2020.
Translation of Decision of Refusal for counterpart JP Application No. 2017-532876, dated Jun. 1, 2020.
Translated First Office Action for counterpart CN Application No. 201680081974.4 dated Jun. 10, 2020.
Translated Second Office Action and Suupplemental Search Report for counterpart CN Application No. 201580076415.X, dated Jun. 17, 2020.
Translated Decision of Rejection for counterpart JP Application No. 2017-532891, dated Jun. 22, 2020.
European Office Action for counterpart Application No. 15 871 083.0-1112, dated Sep. 23, 2020.
Translation of Chinese Office Action for counterpart Application No. 201580076414.5, dated Aug. 21, 2020.
Translation of Chinese Office Action for Application No. 201580076194.6, dated Oct. 12, 2020.
Translation of Brazilian Office Action for counterpart Application No. BR112017012667-2, dated Oct. 28, 2020.
Translation of Brazilian Office Action for counterpart Application No. 11017012615-0, dated Nov. 10, 2020.
Final Office Action for copending U.S. Appl. No. 15/537,122, dated Nov. 13, 2020.
Translated Brazilian Office Action for counterpart Application No. BR112017012836-5, dated Dec. 1, 2020.
Translated Notice of Reasons for Refusal for counterpart JP Application No. 2017-532876, dated Jan. 25, 2021.
Translated Chinese Office Action for counterpart Application No. 201580076442-7, dated Jan. 26, 2021.
Translation of Korean Office Action for counterpart Application No. 10-2017-7019988, dated Feb. 8, 2021.
Translation of Korea Office Action for counterpart Application No. 10-2017-7019991, dated Feb. 23, 2021.
Translation of Chinese Office Action for counterpart Application No. 201580076414.5 dated Mar. 2, 2021.
Non-Final Office Action for copending U.S. Appl. No. 15/537,112, dated Aug. 19, 2021.
Translation of Chinese Office Action for counterpart Application No. 201580076194.6, dated Apr. 23, 2001.
Translation of Brazilian Office Action for counterpart Application No. BR112017012836-5, dated Apr. 19, 2021.
Translation of Japanese Office Action for Application No. 2020-167129, dated Aug. 16, 2021.
Translation of Brazilian Examination Report for Application No. BR112017012836-5, dated Aug. 3, 2021.
Translation of Japanese Office Action for counterpart Application No. 2017-532891, dated Jan. 17, 2022.
Translation of Japanese Office Action for counterpart Application No. 2020-167129, dated Jan. 24, 2022.
Translation of Decision of Dismissal of Amendment for counterpart Japanese Application No. 2020-167129, dated Jan. 24, 2022.
Final Office Action for copending U.S. Appl. No. 15/537,112, dated Feb. 11, 2022.

\* cited by examiner

COMPOSITIONS AND METHODS FOR IMPROVING THE APPEARANCE OF THE SKIN

CROSS REFERENCE TO RELATED APPLICATIONS

This is a national stage application of PCT/US2015/066420, filed internationally on Dec. 17, 2015, which claims priority to U.S. Provisional Application No. 62/093,946, filed Dec. 18, 2014 and French Application Nos. 1462725, 1462731, 1462829, and 1462721, all filed on Dec. 18, 2014, all of which are incorporated by reference herein in their entireties.

TECHNICAL FIELD

The disclosure relates to compositions and methods for improving the appearance of the skin.

BACKGROUND

Skin is primarily comprised of two layers. The outer layer, or epidermis, has a depth of approximately 100 μm. The inner layer, or dermis, has a depth of approximately 3000 μm from the outer surface of the skin and is comprised of a network of fibrous protein known as collagen, which provides skin firmness, and elastin, which supplies skin elasticity and rebound. As a person ages, their skin produces less collagen and elastin each year. As a result, the skin becomes thinner and more fragile with age, and wrinkle formation as a result of aging is inevitable.

In addition, as a person ages, other skin imperfections may appear or become more noticeable. For example, age spots, which are brown or gray sun-induced skin lesions, may appear on sun-exposed skin as a person gets older. It is common for consumers to wish to improve the appearance of such age-related skin imperfections such as wrinkles, crow's feet, age-spots, eye bags, and the like. Additionally, many consumers wish to improve the appearance of, or hide, other skin imperfections such as acne, scars, enlarged pores, and so on, which may not be related to aging.

While topical cosmetic formulations such as foundation or concealer types of make-up may improve the appearance of some skin imperfections, such formulations are not lasting and cannot reduce the appearance of more pronounced skin imperfections, such as deep wrinkles or scars. Further, while some cosmetic formulations may include an ingredient to reduce the appearance of imperfections over time, such as an anti-wrinkle cream, such formulations may take a long time for results to be noticeable, and may also be ineffective to reduce the appearance of more pronounced skin imperfections.

As an alternate to topical cosmetic formulations, more invasive techniques such as surgery, fillers, or laser resurfacing of the skin may provide longer-lasting effects and can treat prominent imperfections. However, many consumers either cannot afford, or do not wish, to undergo such drastic cosmetic treatments.

As such, there is a consumer desire for topical cosmetic formulations that are effective at reducing the appearance of skin imperfections.

SUMMARY

The disclosure relates to compositions and methods for improving the appearance of the skin.

In one embodiment, the disclosure relates to compositions for tightening the skin, said compositions comprising at least one thermoplastic elastomer, at least one adhesive polymer, and at least one filler, wherein the at least one thermoplastic elastomer has at least two glass transition temperatures ($T_g$).

In further embodiments, the disclosure relates to a skin tightening film comprising at least one thermoplastic elastomer, at least one adhesive polymer, and at least one filler, wherein the at least one thermoplastic elastomer has at least two glass transition temperatures ($T_g$), wherein the film has a Young Modulus greater than about 500 kPa.

In yet further embodiments, the disclosure relates to methods for improving the appearance of the skin, said methods comprising forming a film on the skin by applying a composition onto the skin, said composition comprising at least one thermoplastic elastomer, at least one adhesive polymer, and at least one filler, wherein the at least one thermoplastic elastomer has at least two glass transition temperatures ($T_g$), wherein the film has a Young Modulus greater than about 500 kPa.

DETAILED DESCRIPTION

In various embodiments, the disclosure relates to compositions for improving the appearance of the skin. According to various embodiments, the disclosure relates to compositions comprising at least one thermoplastic elastomer, at least one adhesive polymer, and at least one filler.

The compositions may be effective at reducing the appearance of skin imperfections. In various embodiments, the compositions may improve the appearance of the skin by forming a film on the skin that has a Young Modulus greater than that of skin, and thus has the capability of tightening the skin. Additionally, in some embodiments, the film may blur or hide skin imperfections. Accordingly, the disclosure further relates to methods of improving the appearance of the skin by forming a film on the skin with the compositions described herein.

As used herein, the term "long-lasting" means that the film lasts for at least about 6 hours, such as at least about 12 hours, at least about 24 hours, at least about 48 hours, or at least about 72 hours, after the film is formed on the skin.

As used herein, the term "lasting" it is meant to convey that the film is substantially intact in place on the skin.

As used herein, the term "forms quickly" means that the film forms within less than about 20 minutes, such as less than about 15 minutes, or less than about 10 minutes, after the composition is applied to the skin.

As used herein, the term "blur" with regard to skin imperfections means that the visual appearance of the imperfection is less noticeable.

As used herein, the term "tighten" means that the film contracts in a manner that skin has a tighter feel to the user, and that reduces the visual appearance of wrinkles in the skin.

As used herein, the term "soft focus" means that the visual appearance of the skin is more homogenous and matte, leading to the blurring or hiding of skin imperfections.

As used herein, "durable" means the film will not easily rub off, or will not be removed by sweat, water, makeup, lotions, or the like, such that the film will remain substantially intact until removed by the user.

Compositions

According to various embodiments, the compositions comprise at least one thermoplastic elastomer, at least one adhesive polymer, and at least one filler, which together form an association. Additional optional components, such as solvents, silicone elastomers, humectants, water, and pigments, may also be included in the compositions.

Thermoplastic Elastomer

According to various exemplary and non-limiting embodiments, the at least one thermoplastic elastomer may be chosen from block copolymers having at least two glass transition temperatures ("$T_g$"). The block copolymers may be hydrocarbon-soluble or dispersible in the oily phase. In various embodiments, the at least one thermoplastic elastomer may be amorphous, crystalline, or semicrystalline.

The block copolymers comprise one or more hard segments attached to one or more soft segments. The hard segments of the thermoplastic elastomer may comprise vinyl monomers in varying amounts. Examples of suitable vinyl monomers include, but are not limited to, styrene, methacrylate, acrylate, vinyl ester, vinyl ether, vinyl acetate, and the like. The soft segments may comprise olefin polymers and/or copolymers which may be saturated, unsaturated, or combinations thereof. Exemplary olefin copolymers may include, but are not limited to, ethylene/propylene copolymers, ethylene/butylene copolymers, propylene/butylene copolymers, polybutylene, polyisoprene, polymers of hydrogenated butanes and isoprenes, and mixtures thereof.

By way of example, the at least one thermoplastic elastomer may be chosen from diblock, triblock, multiblock, radial, and star copolymers obtained by polymerizing at least one unsaturated hydrocarbon monomer having 2 to 5 carbon atoms and having one or two ethylenic unsaturations. Non-limiting examples of unsaturated hydrocarbon monomers having 2 to 5 unsaturated carbon atoms include ethylene, propylene, butadiene, isoprene or pentadiene. In various exemplary and non-limiting embodiments, block copolymers may be chosen from those comprising at least one styrene block and at least one block comprising units selected from butadiene, ethylene, propylene, butylene, isoprene, or mixtures thereof.

Optionally, the block copolymer may be hydrogenated to reduce the residual ethylenic unsaturation after the polymerization of the monomers. For example, the hydrocarbon-based block copolymer may optionally be a hydrogenated copolymer comprising styrene blocks and ethylene blocks/$C_3$-$C_4$ alkylene or isoprene blocks. In one exemplary embodiment, the block copolymer is an amorphous hydrocarbon block copolymer, for example an amorphous hydrocarbon block copolymer of styrene and monomers of hydrocarbon containing 2 to 5 carbon atoms and comprising one or two ethylenic unsaturations.

The amorphous thermoplastic elastomers comprise at least one first block whose $T_g$ is below about 20° C., such as below about 0° C., below about −20° C., or below about −40° C. The $T_g$ of the first block can, for example, range from about −150° C. to about 20° C., such as from about −100° C. to about 0° C. The block copolymers also comprise at least one second block whose $T_g$ is greater than about 25° C., such as greater than about 50° C., greater than about 75° C., greater than about 100° C., or greater than about 150° C. The $T_g$ of the second block can, for example, range from about 25° C. to about 150° C., such as from about 50° C. to about 125° C., about 60° C. to about 120° C., or about 70° C. to about 100° C.

Exemplary, non-limiting amorphous diblock copolymers may be chosen from styrene-ethylene/propylene copolymers, styrene-ethylene/butadiene copolymers, styrene-ethylene/butylene copolymers, styrene-butadiene, or styrene-isoprene copolymers. Diblock copolymers are sold, for example, under the name Kraton® G1701E by Kraton Polymers.

Exemplary triblock amorphous copolymers may be chosen from styrene-ethylene/propylene-styrene copolymers, styrene-ethylene/butadiene-styrene copolymers, copolymers of styrene-isoprene-styrene, and copolymers of styrene-butadiene-styrene, such as those sold under the names Kraton® G1650, Kraton® D1101, D1102 Kraton®, Kraton® D1160 by Kraton Polymers. In one exemplary embodiment, the thermoplastic elastomer may be a mixture of a triblock copolymer styrene-butylene/ethylene-styrene diblock copolymer and a styrene-ethylene/butylene, such as those sold under the name Kraton® G1657M by Kraton Polymers. In a further example, the thermoplastic elastomer may be a mixture of hydrogenated triblock copolymer styrene-butylene/ethylene-styrene hydrogenated star polymer and ethylene-propylene-styrene, such mixing can in particular be in isododecane in another oil. Such mixtures are sold, for example, by Penreco under the trade names VERSAGEL® M5960 and M5670 VERSAGEL®.

In further exemplary embodiments, the at least one thermoplastic elastomer is chosen from semicrystalline block copolymers having at least two glass transition temperatures. The semicrystalline block copolymers can comprise at least one first block whose $T_g$ is greater than about 40° C., such as greater than about 75° C., or greater than 100° C. The $T_g$ of the first block can, for example, range from about 40° C. to about 150° C., such as from about 50° C. to about 100° C. The semicrystalline block copolymers also comprise at least one second block whose $T_g$ is less than about −50° C., such as less than about −75° C., less than about −100° C., or less than about −150° C. The $T_g$ of the second block can, for example, range from about −150° C. to about −50° C., such as from about −100° C. to about −50° C.

By way of non-limiting example, the semicrystalline thermoplastic elastomers may be chosen from copolymers containing a polyamide and/or a polysilicone and/or a polyurethane, for example polysilicone-polyamides or polysilicone-polyurethanes. For example, the semicrystalline thermoplastic elastomers may be chosen from polyorganosiloxane-containing polymers comprising at least one moiety corresponding to formula I:

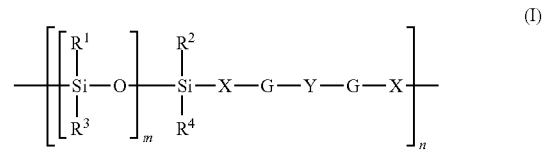

in which:

1) $R^1$, $R^2$, $R^3$ and $R^4$, which may be identical or different, represent a group chosen from: (a) linear, branched or cyclic, saturated or unsaturated, $C_1$ to $C_{40}$ hydrocarbon-based groups, possibly containing in their chain one or more oxygen, sulphur and/or nitrogen atoms, and possibly being partially or totally substituted with fluorine atoms, (b) $C_6$ to $C_{10}$ aryl groups, optionally substituted with one or more $C_1$ to $C_4$ alkyl groups, (c) polyorganosiloxane chains possibly containing one or more oxygen, sulphur and/or nitrogen atoms;

2) X, which may be identical or different, represents a linear or branched $C_1$ to $C_{30}$ alkylenediyl group, possibly containing in its chain one or more oxygen and/or nitrogen atoms;

3) Y is a saturated or unsaturated, $C_1$ to $C_{50}$ linear or branched divalent alkylene, arylene, cycloalkylene, alkylarylene or arylalkylene group, optionally comprising one or more oxygen, sulphur and/or nitrogen atoms, and/or optionally substituted with one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with one to three $C_1$ to $C_3$ alkyl, $C_1$ to $C_3$ hydroxyalkyl, and $C_1$ to $C_6$ aminoalkyl groups;

4) G, which may be identical or different, represents a group chosen from ester, amide, sulphonamide, carbamate, thiocarbamate, urea, thiourea groups, and combinations thereof;

5) m is an integer ranging from 1 to 1,000, preferably from 1 to 700 and more preferably from 6 to 200; and 6) n is an integer ranging from 2 to 500 and preferably from 2 to 200.

In further embodiments, the semicrystalline thermoplastic elastomers may be chosen from copolymers containing at least one moiety corresponding to formula II:

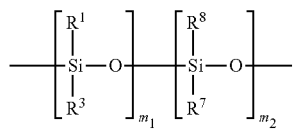

(II)

in which:

$R^1$ and R, which may be identical or different, are as defined above for formula (I), $R^7$ represents a group as defined above for $R^1$ and $R^3$, or represents a group of formula —X-G-$R^9$ in which X and G are as defined above for formula (I) and $R^9$ represents a hydrogen atom or a linear, branched or cyclic, saturated or unsaturated, $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups, $R^8$ represents a group of formula —X-G-$R^9$ in which X, G and $R^9$ are as defined above, $m_1$ is an integer ranging from 1 to 998, and $m_2$ is an integer ranging from 2 to 500.

In yet further embodiments, it is also possible to use a block copolymer comprising several different moieties of formula (I), and/or several different moieties of formula (II), for example a polymer in which at least one of the groups $R^1$, $R^2$, $R^3$, $R^4$, X, G, Y, m, and n is different in one of the moieties. It is also possible to use a block copolymer comprising at least one moiety of formula (I) and at least one moiety of formula (II), the moieties of formula (I) and the moieties of formula (II) possibly being identical to, or different from, each other.

For example, in at least one embodiment, the semicrystalline thermoplastic elastomer may be chosen from polyamide copolymers containing at least one moiety corresponding to formula III and at least one moiety corresponding to formula IV:

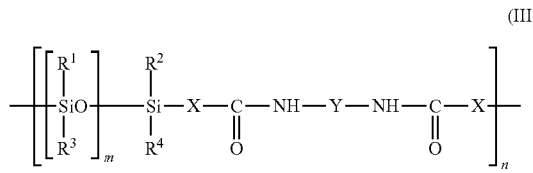

(III)

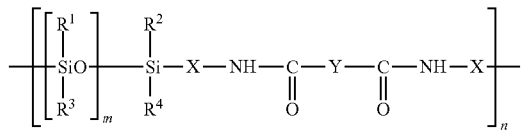

(IV)

in which:

(a) $R^1$, $R^2$, $R^3$, and $R^4$ are the same or different and may be selected from the group consisting of methyl, ethyl, propyl, isopropyl, a siloxane chain, and phenyl;

(b) X is a linear or branched chain alkylene having 1-30 carbons;

(c) Y is selected from the group consisting of linear or branched chain alkylenes having 1-40 carbons;

(d) m is a number between 1 and 700; and (e) n is a number between 1 and 500.

By way of example only, the semicrystalline thermoplastic elastomer may be chosen from Nylon 6, Nylon 66, and Nylon-611/dimethicone copolymer.

The thermoplastic elastomer may be present in the composition in an amount up to about 25%, such as an amount ranging from about 5% to about 20%, about 6% to about 18%, about 7% to about 16%, about 8% to about 15%, about 9% to about 14%, relative to the weight of the composition.

Adhesive Polymer

Compositions according to the disclosure further comprise at least one adhesive film-forming polymer. In various embodiments, the at least one adhesive polymer may be amorphous, crystalline, or semicrystalline.

In various embodiments, the adhesive polymer may have a $T_g$ greater than about 25° C., such as greater than about 50° C., greater than about 75° C., or greater than about 100° C., according to various embodiments. In further embodiments, the adhesive polymer may have a $T_g$ less than about 25° C., such as less than about 0° C., less than about −25° C., or less than about −50° C.

The at least one adhesive polymer may be present in the composition in an amount up to about 25%, such as an amount ranging from about 5% to about 20%, about 6% to about 18%, about 7% to about 16%, about 8% to about 15%, about 9% to about 14%, or relative to the weight of the composition.

As non-limiting examples of adhesive polymers having a $T_g$ greater than about 25° C. may be mentioned polymer particles of $C_1$-$C_4$ alkyl(methacrylate)polymer, stabilized in a non-aqueous dispersion, referred to herein for ease of reference as an "oil dispersion," such as those described in WO2015/091513 which is incorporated by reference herein.

By way of example, the $C_1$-$C_4$ alkyl (meth)acrylate monomers may be chosen from methyl (meth)acrylate, ethyl (meth)acrylate, n-propyl (meth)acrylate, isopropyl (meth)acrylate, n-butyl (meth)acrylate and tert-butyl (meth)acrylate. For example, the polymer may be a methyl acrylate and/or ethyl acrylate polymer.

The polymer may also comprise an ethylenically unsaturated acid monomer or the anhydride thereof, chosen especially from ethylenically unsaturated acid monomers comprising at least one carboxylic, phosphoric or sulfonic acid function, such as crotonic acid, itaconic acid, fumaric acid, maleic acid, maleic anhydride, styrenesulfonic acid, vinylbenzoic acid, vinylphosphoric acid, acrylic acid, methacrylic acid, acrylamidopropanesulfonic acid or acrylamidoglycolic acid, and salts thereof. For example, the ethylenically unsaturated acid monomer may be chosen from (meth) acrylic acid, maleic acid, and maleic anhydride.

The salts may be chosen from salts of alkali metals, for example sodium or potassium; salts of alkaline-earth metals, for example calcium, magnesium or strontium; metal salts, for example zinc, aluminum, manganese or copper; ammonium salts of formula NH$^+$; quaternary ammonium salts; salts of organic amines, for instance salts of methylamine, dimethylamine, trimethylamine, triethylamine, ethylamine, 2-hydroxyethylamine, bis(2-hydroxyethyl)amine or tris(2-hydroxyethyl)amine; lysine or arginine salts.

The polymer of the particles of the oil dispersion may thus comprise or consist essentially of about 80% to about 100%, by weight, of $C_1$-$C_4$ alkyl (meth)acrylate and of about 0% to about 20%, by weight, of ethylenically unsaturated acid monomer, relative to the total weight of the polymer. According to one exemplary embodiment, the polymer consists essentially of a polymer of one or more $C_1$-$C_4$ alkyl (meth)acrylate monomers. According to another exemplary embodiment, the polymer consists essentially of a copolymer of $C_1$-$C_4$ (meth)acrylate and of (meth)acrylic acid or maleic anhydride.

By way of non-limiting example only, the polymer of the particles in the oil dispersion, which may optionally be crosslinked or alternatively may not be crosslinked, may be chosen from methyl acrylate homopolymers, ethyl acrylate homopolymers, methyl acrylate/ethyl acrylate copolymers, methyl acrylate/ethyl acrylate/acrylic acid copolymers, methyl acrylate/ethyl acrylate/maleic anhydride copolymers, methyl acrylate/acrylic acid copolymers, ethyl acrylate/acrylic acid copolymers, methyl acrylate/maleic anhydride copolymers, and ethyl acrylate/maleic anhydride copolymers.

The polymer of the particles in the dispersion may have a number-average molecular weight ranging from about 2000 to about 10,000,000, for example ranging from about 150,000 to about 500,000. The polymer particles may be present in the oil dispersion in a content ranging from about 20% to about 60%, for example about 21% to about 58.5%, about 30% to about 50%, about 35% to about 45%, or about 36% to about 42%, by weight, relative to the total weight of the oil dispersion.

The stabilizer in the oil dispersion may be an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than about 4, for example greater than about 4.5, or greater than about 5. For example, the weight ratio may range from about 4.5 to about 19, such as from about 5 to about 19, or from about 5 to about 12.

By way of example only, the stabilizer may be chosen from isobornyl acrylate homopolymers, statistical copolymers of isobornyl acrylate/methyl acrylate, statistical copolymers of isobornyl acrylate/methyl acrylate/ethyl acrylate, and statistical copolymers of isobornyl methacrylate/methyl acrylate.

In various embodiments, the stabilizer may have a number-average molecular weight ranging from about 10,000 to about 400,000, such as from about 20,000 to about 200,000.

In various embodiments, the combination of the stabilizer+polymer of the particles present in the oil dispersion comprises from about 10% to about 50%, such as about 15% to about 30%, by weight of polymerized isobornyl (meth)acrylate, and from about 50% to about 90%, such as about 70% to about 85%, by weight of polymerized $C_1$-$C_4$ alkyl (meth)acrylate, relative to the total weight of the combination of the stabilizer+polymer of the particles.

The oily medium of the oil dispersion comprises a hydrocarbon-based oil. The hydrocarbon-based oil is an oil that is liquid at room temperature (25° C.). The term "hydrocarbon-based oil" means an oil formed essentially from, or even consisting of, carbon and hydrogen atoms, and optionally oxygen and nitrogen atoms, and not containing any silicon or fluorine atoms. It may contain alcohol, ester, ether, carboxylic acid, amine and/or amide groups.

Exemplary and non-limiting embodiments of the hydrocarbon-based oil medium of the oil dispersion include hydrocarbon-based oils containing up to about 40, such as from 8 to 16 or from 8 to 14, carbon atoms. Optionally, the hydrocarbon-based oil is apolar. For example, the hydrocarbon based oil may be chosen from isododecane.

The oil dispersion may be prepared, for example, as described in WO2015/091513.

Alternatively, the adhesive polymer may be chosen from aliphatic or cycloaliphatic hydrocarbon polymers selected from aliphatic or cycloaliphatic hydrocarbon resins having a $T_g$ greater than about 25° C. By "aliphatic or cycloaliphatic hydrocarbon resins," it is meant polymers or copolymers of olefins or polymers or copolymers of partly or totally hydrogenated aromatic hydrocarbon monomers. For example, the adhesive polymer may be chosen from aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, polyterpenes, aromatic modified polyterpenes, terpene phenolics, aromatic modified hydrogenated polycyclopentadiene resins, hydrogenated aliphatic resin, hydrogenated aliphatic aromatic resins, hydrogenated terpenes and modified terpenes, hydrogenated rosin acids, hydrogenated rosin esters, polyisoprene, partially or fully hydrogenated polyisoprene, polybutenediene, partially or fully hydrogenated polybutenediene, and hydrogenated styrene/methyl styrene/indene copolymers. In various embodiments, hydrogenated indene/methylstyrene/styrene copolymers marketed under the name of REGALITE® by Eastman Chemical, may be chosen. For example, REGALITE® R1090, REGALITE® R1100, REGALITE® S1100, REGALITE® R7100, REGALITE® R1010, REGALITE® R112, or REGALITE® S5100 may be chosen. As further examples, those sold under the name of ARKON® P-90, ARKON® P-100, and ARKON® P-115, by Arakawa, may be chosen.

In further embodiments, the adhesive polymer may have a $T_g$ of less than about 25° C. For example, the at least one adhesive polymer may be chosen from polyacids, such as hyperbranched polyacids. Polyacids useful according to various embodiments of the disclosure may be found in U.S. Pat. No. 7,582,719 and US2013/0236409, both of which are incorporated by reference herein.

The term "hyperbranched polyacid" refers to the fact that the functional groups of the hyperbranched functional polymer are substituted with carboxylic acid groups. Unsaturated functionalizing compounds useful include, but are not limited to, carboxylic acids, carboxylic acid esters, amides, ethers, amines, phosphate esters, silanes and alcohols. Examples of such carboxylic acids include, but are not limited to, 5-hexenoic acid, 6-heptenoic acid, 10-undecylenic acid, 9-decenoic acid, oleic acid, and erucic acid. Also useful are esters of these acids with linear or branched-chain alcohols having from about 1 to about 10 carbon atoms, as well as triglycerides containing olefinic unsaturation in the fatty acid portion such as tall oil, fish oils, soybean oil, linseed oil, cottonseed oil and partially hydrogenated products of such oils. Other useful materials include olefinic alcohols such as allyl alcohol, 9-decen-1-ol, 10-undecylenyl alcohol, oleyl alcohol, erucyl alcohol, acetic acid or formic acid esters of these alcohols, C1-C4 alkyl ether derivatives of these alcohols and formamides or acetamides of unsaturated amines such as oleylamine, erucylamine, 10-undecylenylamine and allylamine.

In various embodiments, the hyperbranched polyacid compound useful according to the disclosure may have at least two carboxyl groups. In various embodiments, the hyperbranched polyacid has a carboxyl number of at least 3, such as at least 10, at least 50, at least 100, or at least about 150. According to various embodiments, the hyperbranched polyacid has a carboxyl number ranging from about 50 to about 250, such as ranging from about 75 to about 225, about 100 to about 200, or about 125 to 175. In one embodiment, the hyperbranched polyacid has a carboxyl number ranging from 90 to 150.

In various embodiments, the at least one hyperbranched acid compound has a molecular weight (Mw) ranging from about 500 to about 25,000, such as ranging from about 800 to about 10,000, or from about 1000 to about 8000. In one embodiment, the hyperbranched polyacid has a Mw ranging from about 1000 to about 6000.

In various embodiments, the at least one hyperbranched polyacid compound has a viscosity at 210° F. ranging from 0.01 Pas to 10 Pas, such as from 0.02 to 7 Pas, or from 0.03 to 6 Pas, including all ranges and subranges there between. The viscosity is determined using Brookfield viscometer at 210° F. by ASTMD-3236MOD method. In various embodiments, the at least one hyperbranched acid compound has an acid number ranging from about 20 to about 400 mg/KOH, such as from about 30 to about 300 mg/KOH, or ranging from about 50 to about 100 mg/KOH.

In one exemplary embodiment, the at least one adhesive polymer is a polyacid chosen from $C_{30+}$ olefin/undecylenic acid copolymers, such as $C_{28}$-$C_{52}$ olefin/undecylenic acid copolymers, for example those available from New Phase Technologies under trade name Performa V6112™.

As yet further examples of adhesive polymers that may be chosen are acrylic type film formers. As used herein, "acrylic type film formers" include polymers that are film forming agents and which are based upon one or more (meth)acrylic acid (and corresponding (meth)acrylate) monomers or similar monomers.

Non-limiting examples of such film forming agents include copolymers containing at least one apolar monomer, at least one olefinically unsaturated monomer, and at least one vinylically functionalized monomer.

For the apolar monomers, acrylic monomers which comprise acrylic and methacrylic esters with alkyl groups composed of 4 to 14 C atoms, preferably 4 to 9 C atoms may be chosen. Examples of monomers of this kind include n-butyl acrylate, n-butyl methacrylate, n-pentyl acrylate, n-pentyl methacrylate, n-amyl acrylate, n-hexyl acrylate, hexyl methacrylate, n-heptyl acrylate, n-octyl acrylate, n-octyl methacrylate, n-nonyl acrylate, isobutyl acrylate, isooctyl acrylate, isooctyl methacrylate, and their branched isomers, such as, for example, 2-ethylhexyl acrylate, 2-ethylhexyl methacrylate.

For olefinically unsaturated monomers, it is possible to use monomers having functional groups selected from hydroxyl, carboxyl, sulphonic acid groups, phosphonic acid groups, acid anhydrides, epoxides, and amines. Examples of olefinically unsaturated monomers include acrylic acid, methacrylic acid, itaconic acid, maleic acid, fumaric acid, crotonic acid, aconitic acid, dimethylacrylic acid, beta-acryloyloxypropionic acid, trichloracrylic acid, vinylacetic acid, vinylphosphonic acid, itaconic acid, maleic anhydride, hydroxyethyl acrylate, hydroxypropyl acrylate, hydroxyethyl methacrylate, hydroxypropyl methacrylate, 6-hydroxyhexyl methacrylate, allyl alcohol, glycidyl acrylate, glycidyl methacrylate.

For vinylically functionalized compounds, exemplary monomers include monomers which are copolymerizable with one or both of the previously discussed monomers and include, for example, methyl acrylate, ethyl acrylate, propyl acrylate, methyl methacrylate, ethyl methacrylate, benzyl acrylate, benzyl methacrylate, sec-butyl acrylate, tert-butyl acrylate, phenyl acrylate, phenyl methacrylate, isobornyl acrylate, isobornyl methacrylate, tert-butylphenyl acrylate, tert-butylphenyl methacrylate, dodecyl methacrylate, isodecyl acrylate, lauryl acrylate, n-undecyl acrylate, stearyl acrylate, tridecyl acrylate, behenyl acrylate, cyclohexyl methacrylate, cyclopentyl methacrylate, phenoxyethyl acrylate, phenoxyethyl methacrylate, 2-butoxyethyl methacrylate, 2-butoxyethyl acrylate, 3,3,5-trimethylcyclohexyl acrylate, 3,5-dimethyladamantyl acrylate, 4-cumylphenyl methacrylate, cyanoethyl acrylate, cyanoethyl methacrylate, 4-biphenyl acrylate, 4-biphenyl methacrylate, 2-naphthyl acrylate, 2-naphthyl methacrylate, tetrahydrofurfuryl acrylate, diethylaminoethyl acrylate, diethylaminoethyl methacrylate, dimethylaminoethyl acrylate, dimethylaminoethyl methacrylate, 2-butoxyethyl acrylate, 2-butoxyethyl methacrylate, methyl 3-methoxyacrylate, 3-methoxybutyl acrylate, phenoxyethyl acrylate, phenoxyethyl methacrylate, 2-phenoxyethyl methacrylate, butyldiglycol methacrylate, ethylene glycol acrylate, ethylene glycol monomethylacrylate, methoxy-polyethylene glycol methacrylate 350, methoxy-polyethylene glycol methacrylate 500, propylene glycol monomethacrylate, butoxydiethylene glycol methacrylate, ethoxytriethylene glycol methacrylate, octafluoropentyl acrylate, octafluoropentyl methacrylate, 2,2,2-trifluoroethyl methacrylate, 1,1,1,3,3,3-hexafluoroisopropyl acrylate, 1,1,1,3,3,3-hexafluoroisopropyl methacrylate, 2,2,3,3,3-pentafluoropropyl methacrylate, 2,2,3,4,4,4-hexafluorobutyl methacrylate, 2,2,3,3,4,4,4-heptafluorobutyl acrylate, 2,2,3,3,4,4,4-heptafluorobutyl methacrylate, 2,2,3,3,4,4,5,5,6,6,7,7,8,8,8-pentadecafluorooctyl methacrylate, dimethylaminopropylacrylamide, dimethylaminopropylmethacrylamide, N-(1-methylundecyl)acrylamide, N-(n-butoxymethyl)acrylamide, N-(butoxymethyl)methacrylamide, N-(ethoxymethyl)acrylamide, N-(n-octadecyl)acrylamide, and also N,N-dialkyl-substituted amides, such as, for example, N,N-dimethylacrylamide, N,N-dimethylmethacrylamide, N-benzylacrylamides, N-isopropylacrylamide, N-tert-butylacrylamide, N-tert-octylacrylamide, N-methylolacrylamide, N-methylolmethacrylamide, acrylonitrile, methacrylonitrile, vinyl ethers, such as vinyl methyl ether, ethyl vinyl ether, vinyl isobutyl ether, vinyl esters, such as vinyl acetate, vinyl chloride, vinyl halides, vinylidene chloride, vinylidene halide, vinylpyridine, 4-vinylpyridine, N-vinylphthalimide, N-vinyllactam, N-vinylpyrrolidone, styrene, a- and p-methylstyrene, a-butylstyrene, 4-n-butylstyrene, 4-n-decylstyrene, 3,4-dimethoxystyrene, macromonomers such as 2-polystyrene-ethyl methacrylate (molecular weight, Mw, of 4000 to 13 000 g/mol), poly(methyl methacrylate)ethyl methacrylate (Mw of 2000 to 8000 g/mol).

As exemplary acrylic type film formers, mention may be made of copolymers of acrylic acid, isobutyl acrylate and isobornyl acetate, such as that sold under the names Pseudoblock (Chimex) and Synamer-3. In both of these commercial products, the copolymer is present with a solvent in a 1:1 ratio (50% solid). Another exemplary film former is Poly (isobornyl methacrylate-8 co-isobornyl acrylate-co-isobutyl acrylate-co-acrylic acid) at 50% of active material in 50% of octyldodecyl neopentanoate (Mexomere PAZ from Chimex).

Fillers

The compositions comprise at least one filler. The fillers may be mineral or organic in nature, and of any shape. In various embodiments, the fillers may have a particle size greater than about 100 nm, and/or a specific surface area greater than about 200 m$^2$/g.

By way of non-limiting example, fillers may be chosen from talc, mica, silica, silica surface-treated with a hydrophobic agent, fumed silica, kaolin, polyamide (Nylon®) powders (e.g. Orgasol® from Atochem), polyurethane powders, poly-β-alanine powder and polyethylene powder, powders of tetrafluoroethylene polymers (Teflon®), lauroyllysine, starch, boron nitride, hollow polymer microspheres such as those of polyvinylidene chloride/acrylonitrile, for instance Expancel® (Nobel Industrie) or of acrylic acid copolymers (Polytrap® from the company Dow Corning) and silicone resin microbeads (Tospearls® from Toshiba, for example), elastomeric polyorganosiloxane particles, precipitated calcium carbonate, magnesium carbonate, magnesium hydrogen carbonate, hydroxyapatite, hollow silica microspheres (Silica Beads® from Maprecos), glass or ceramic microcapsules, and metal soaps derived from organic carboxylic acids containing from 8 to 22 carbon atoms and preferably from 12 to 18 carbon atoms, for example zinc stearate, magnesium stearate or lithium stearate, zinc laurate or magnesium myristate.

In at least certain embodiments, the at least one filler may be chosen from hydrophobic silica aerogel particles. Silica aerogels are porous materials obtained by replacing (by drying) the liquid component of a silica gel with air. Hydrophobic silica aerogel particles useful according to embodiments of the disclosure include silylated silica (INCI name: silica silylate) aerogel particles. The preparation of hydrophobic silica aerogel particles that have been surface-modified by silylation is described more fully in U.S. Pat. No. 7,470,725, incorporated by reference herein.

In various embodiments, aerogel particles of hydrophobic silica surface-modified with trimethylsilyl groups may be chosen. For example, the aerogel sold under the name VM-2260® by the company Dow Corning, the particles of which have an average size of about 1000 microns and a specific surface area per unit of mass ranging from 600 to 800 m$^2$/g, or the aerogel sold under the name VM-2270®, also by the company Dow Corning, the particles of which have an average size ranging from 5 to 15 microns and a specific surface area per unit of mass ranging from 600 to 800 m$^2$/g, may be chosen. In other embodiments, the aerogels sold by the company Cabot under the names Aerogel TLD 201®, Aerogel OGD 201®, and Aerogel TLD 203®, CAB-O-SIL TS-530, CAB-O-SIL TS-610, CAB-O-SIL TS-720, Enova Aerogel MT 1100®, and Enova Aerogel MT 1200®, may be chosen.

Optionally, mixtures of fillers may be present in the compositions according to the disclosure. For example, a mixture of different aerogel particles, or of an aerogel and a different type of filler, may be used.

The at least one filler may be present in a total amount ranging from about 0.1% to about 20% by weight, for example from about 0.2% to about 15%, from about 0.5% to about 10%, or from about 1% to about 6%, by weight, relative to the total weight of the composition. In at least certain exemplary embodiments, the filler is present in an amount less than about 5%, such as less than about 4%, by weight, relative to the total weight of the composition. In one embodiment, the filler is present in an amount up to about 3% by weight, relative to the total weight of the composition.

Additional Components

The compositions according to the disclosure may optionally further comprise additional components, such as solvents, silicone elastomers, humectants, water, and pigments.

Solvents

The compositions may comprise at least one solvent. Optionally, the compositions may comprise at least one solvent chosen from solvents having a vapor pressure at room temperature (25° C.) of greater than about 100 Pa, such as greater than about 500 Pa, or greater than about 1000 Pa. In various embodiments, the composition is free or substantially free of solvents having a vapor pressure at room temperature (25° C.) of less than about 25 Pa. In further embodiments, the composition may comprise at least one solvent having a vapor pressure at room temperature (25° C.) of greater than about 100 Pa, such as greater than 500 Pa, or greater than 1000 Pa, and at least one solvent having a vapor pressure at room temperature (25° C.) of less than about 100 Pa, such as less than about 50 Pa, or less than about 25 Pa.

In various embodiments, the compositions comprise at least one volatile organic solvent. The volatile organic solvent may be chosen from, for example, volatile hydrocarbon-based oils and volatile silicone oils.

For example, volatile hydrocarbon oils include, but are not limited to, those having from 8 to 16 carbon atoms and their mixtures, such as branched $C_8$ to $C_{16}$ alkanes and $C_8$ to $C_{16}$ isoalkanes (also known as isoparaffins), isododecane, isodecane, isohexadecane. For example, the at least one solvent may be chosen from the oils sold under the trade names of Isopar® or Permethyl®, the $C_8$ to $C_{16}$ branched esters such as isohexyl or isodecyl neopentanoate and their mixtures. In at least certain embodiments, the volatile hydrocarbon oils have a flash point of at least 40° C. It is also possible to use mixtures of isoparaffins and other volatile hydrocarbon-based oils, such as petroleum distillates.

Further, volatile silicone oils may be chosen from linear or cyclic silicone oils, such as those having a viscosity at room temperature (25° C.) of less than or equal to 6 cSt and having from 2 to 7 silicon atoms, these silicones being optionally substituted with alkyl or alkoxy groups of 1 to 10 carbon atoms. Examples of volatile silicone oils that may be used include, but are not limited to, octamethyltetrasiloxane, decamethylcyclo-pentasiloxane, dodecamethylcyclohexasiloxane, heptamethyloctyltrisiloxane, hexamethyldisiloxane, decamethyltetrasiloxane, dodecamethylpentasiloxane, and their mixtures. In at least certain embodiments, the volatile silicone oils have a flash point of at least 40° C.

Additionally, the at least one volatile solvent may be chosen from polar volatile solvents, including but are not limited to, alcohols, volatile esters and volatile ethers.

The at least one solvent may be present in the composition in an amount up to about 95%, such as up to about 90%, up to about 85%, up to about 80%, up to about 75%, up to about 70%, up to about 65%, up to about 60%, up to about 55%, or up to about 50%, by weight of the composition. For example, the at least one solvent may be present in the composition in an amount ranging from about 40% to about 95%, such as about 50% to about 90%, or about 60% to about 85%, or about 65% to about 80%.

Silicone Elastomer

The composition may further optionally comprise at least one silicone elastomer. Surprisingly, in certain embodiments, the at least one silicone elastomer may improve properties such as the thickness and water-resistance of the film, without significantly affecting the mechanical or optical properties of the film. In other embodiments, the addition of at least one silicone elastomer may decrease wettability by sebum, which will help prevent the film from losing tightening properties. It may, in at least certain embodiments, be advantageous to choose a silicone elastomer having greater than 1% active material (AM), such as greater than 2% AM.

The at least one silicone elastomer may, for example, be chosen from at least one silicone crosspolymer dispersed in at least one oil. The at least one silicone crosspolymer may, in certain embodiments, be chosen from dimethicone crosspolymers, such as dimethicone/vinyl dimethicone crosspolymers and dimethicone/phenyl vinyl dimethicone crosspolymers. In other embodiments, the silicone crosspolymer may be modified by one or more groups chosen from alkyl, polyether, polyglycerin groups. For instance, the alkyl modified silicone cross-polymers may be chosen from vinyl dimethicone/lauryl dimethicone cross-polymers, cetearyl dimethicone cross-polymers, and $C_{30}$-$C_{45}$ alkyl cetearyl dimethicone cross-polymers. Non-limiting examples of polyether modified silicone cross-polymers include dimethicone/PEG-10/15 cross-polymers. Exemplary alkyl and polyether modified silicone cross-polymers may be chosen, for example, from PEG-10/lauryl dimethicone cross-polymers and PEG-15/lauryl dimethicone cross-polymers. Exemplary polyglycerin modified silicone cross-polymers include dimethicone/polyglycerin-3 cross-polymers and lauryl dimethicone/polyglycerin-3 cross-polymers.

In at least certain embodiments, the silicone polymers do not comprise polyethylene glycol or polypropylene groups, or hydrophilic moieties. Optionally, the silicone elastomer may be chosen from the silicone organic blends isododecane (and) dimethicone crosspolymer (18% AM) sold under the name EL-8040 ID or dimethicone/bis-isobutyl PPG-20 crosspolymer (17% AM in isododecane) sold under the name EL-8050 ID, by Dow Corning; or isododecane (and) vinyldimethyl/trimethylsiloxysilicate stearyl dimethicone crosspolymer (20% AM in isododecane), sold under the name GEL BELSIL RG90 by Wacker.

The silicone crosspolymer may be dispersed in at least one oil. In certain embodiments, the oil may be chosen from silicone oils, such as cyclic and linear organopolysiloxanes. Cyclic organopolysiloxanes may include, for example, cyclotetrasiloxane; cyclopentasiloxane; and methylated cyclic organopolysiloxanes, for example, octamethylcyclotetrasiloxane and decamethylcyclopentasiloxane. Non-limiting examples of linear organopolysiloxanes include low molecular weight dimethicones; high molecular weight dimethicones; alkyl derivatives of linear organopolysiloxanes, for example, cetyl dimethicone and lauryl trimethicone; aryl derivatives of linear organopolysiloxanes, for example, phenyl trimethicone; and hydroxylated derivatives of linear organopolysiloxanes, for example, dimethiconol. In other embodiments, the oil may be chosen from organic oils, such as mineral oil; linear and branched alkanes, for example, isododecane; triethylhexanoin; and squalane.

The at least one silicone crosspolymer may, in some embodiments, comprise from about 5% to about 35% by weight, relative to the total weight of the silicone elastomer blend, for example, from about 10% to about 20% by weight, or from about 25% to about 35% by weight, or from about 20% to about 30% by weight. The at least one oil may comprise from about 65% to about 95% by weight, relative to the total weight of the silicone elastomer blend, such as from about 80% to about 90% by weight, or from about 65% to about 75% by weight, or from about 70% to about 80% by weight.

In various exemplary embodiments, the silicone elastomer blend comprises from about 20% to about 30% of dimethicone/vinyl dimethicone cross-polymer. In further exemplary embodiments, the silicone elastomer blend comprises from about 70% to about 80% by weight of dimethicone. In yet further exemplary embodiments, the silicone elastomer blend comprises from about 20% to about 30% of dimethicone/vinyl dimethicone cross-polymer and from about 70% to about 80% by weight dimethicone.

For example, silicone elastomers sold under the name KSG-16 dimethicone (and) dimethicone/vinyl dimethicone corpsspolymer, KSG-21 (at 27% in active material) INCI name: Dimethicone/PEG-10 Dimethicone vinyl dimethicone crosspolymer), KSG-20 (at 95% % in active material) INCI name: PEG-10 Dimethicone Crosspolymer), KSG-30, (at 100% % in active material) INCI name: Lauryl PEG-15 Dimethicone vinyl dimethicone crosspolymer), KSG-31 (at 25% in active material) INCI name: Lauryl PEG-15 Dimethicone vinyl dimethicone crosspolymer), KSG-32 or KSG-42 or KSG-320 or KSG-30 (at 25% in active material) INCI name: Lauryl PEG-15 Dimethicone vinyl dimethicone crosspolymer), KSG-33: Lauryl PEG-15 (at 20% in active material) Dimethicone vinyl dimethicone crosspolymer), KSG-210 (at 25% in active material) INCI name: Dimethicone/PEG-10/15 crosspolymer), KSG-310: lauryl modified polydimethylsiloxane polyoxyethylenated in mineral oil, KSG-330 and KSG-340: PEG-15/lauryl dimethicone crosspolymer, and X-226146 (at 32% % in active material) INCI name: Dimethicone/PEG-10 Dimethicone vinyl dimethicone crosspolymer), all by Shin Etsu; DC9010 (at 9% in active material) and DC9011 (at 11% in active material) INCI name: PEG-12 dimethicone crosspolymer), DC9040 cyclopentasiloxane (and) dimethicone crosspolymer, and DC9041 dimethicone (and) dimethicone crosspolymer, all by Dow Corning; or the products sold under the VELVESIL product line by Momentive, such as VELVESIL 125 and VELVESIL DM, may be chosen.

Other examples of silicone elastomers include KSG-710 (at 25% in active material, INCI name: dimethicone/polyglycerin-3 crosspolymer); and KSG-820, KSG-830 and KSG-840, all of which are dimethicone/polvaleverin-3 crosspolymer (INCI), but in different diluents, 820 is in isododecane, 830 is in triethyl hexanoin, and 840 is in squalene, all by Shin Estu.

The at least one silicone elastomer may optionally be included in the composition in an amount up to about 10%, such as up to about 8%, up to about 5%, about 4.5%, up to about 4%, up to about 3.5%, up to about 3%, up to about 2.5%, up to about 2%, up to about 1.5%, up to about 1%, up to about 0.75%, up to about 0.5%, up to about 0.25%, up to about 0.2%, or up to about 0.1%, by weight, relative to the weight of the composition. In certain embodiments, the at least one silicone elastomer may be present in an amount ranging from about 1% to about 10%, such as about 2% to about 8%, about 3% to about 6%, or about 4% to about 5%, by weight, relative to the weight of the composition.

Humectants

Optionally, compositions according to the disclosure may comprise at least one humectant or moisturizing agent. Surprisingly, in at least certain embodiments, the at least one humectant may improve the optical properties and feeling of the film formed on the skin by the composition, without negatively affecting the mechanical properties of the film.

By way of example only, humectants or moisturizing agents may be chosen from polyhydroxy compounds including but not limited to glycerin and glycols such as, for example, propylene glycol, butylene glycol, dipropylene glycol and diethylene glycol, glycol ethers such as monopropylene, dipropylene and tripropylene glycol alkyl($C_1$-$C_4$) ethers, monoethylene, diethylene and triethylene glycol.

The at least one humectant may be present in the composition in an amount up to about 20%, such as up to about 15%, up to about 14%, up to about 13%, up to about 12%, up to about 11%, up to about 10%, up to about 9%, up to about 8%, up to about 7%, up to about 6%, up to about 5%, up to about 4%, up to about 3%, up to about 2%, up to about 1%, or up to about 0.5%, by weight of the composition.

Water

Optionally, in at least certain embodiments, water may be added to the compositions according to the disclosure. Surprisingly, in certain non-limiting embodiments, water may improve the properties of the film formed on the skin by the composition, such as Young Modulus, transparency, cohesion, and thickness.

Water can be included in the composition in an amount up to about 15%, up to about 12%, up to about 10%, up to about 9%, up to about 8%, up to about 7%, up to about 6%, up to about 5%, up to about 4%, up to about 3%, up to about 2%, up to about 1%, or up to about 0.5%, by weight of the composition. In at least certain embodiments, the compositions are anhydrous or substantially anhydrous. In other embodiments, the compositions may be in the form of a water-in-oil (W/O) emulsion.

It may, in at least certain embodiments, be advantageous to include water and at least one humectant, for example water and glycerin, in the composition together.

Colorants

The composition may further include at least one colorant, for example to create a colored film on the skin, which may be useful to hide certain skin imperfections. In various embodiments, the at least one colorant may be chosen from dyes, pigments, and nacres.

The at least one colorant may, for example, be chosen from dyes. Non-limiting examples of dyes include Sudan Red, D & C Red 17, D & C Green 6, β-carotene, soybean oil, Sudan Brown, D & C Yellow 11, D & C Violet 2, D & C Orange 5, quinoline yellow and annatto.

In various embodiments, the at least one colorant may be chosen from pigments. As used herein, the term "pigments" is intended to mean white or colored, mineral or organic particles which are insoluble in the composition in which they are present, and which are intended to color and/or opacify the resulting film.

By way of example, inorganic pigments that may be used include titanium oxides, zirconium oxides, cerium oxides, zinc oxides, iron oxides, chromium oxides, ferric blue, manganese violet, ultramarine blue, and chromium hydrate. For example, pigments may be chosen from titanium dioxide and red, black, and/or yellow iron oxide, as well as mixtures thereof.

In further embodiments, pigments with a structure that may be, for example, of silica microspheres containing iron oxide type, may be used. An example of a pigment having this structure is the product sold by the company Miyoshi under the reference PC Ball PC-LL-100 P, constituted of silica microspheres containing yellow iron oxide.

By way of further example, organic pigments that may be used include nitroso, nitro, azo, xanthene, pyrene, quinoline, anthraquinone, triphenylmethane, fluorane, phthalocyanin, metal complex, isoindolinone, isoindoline, quinacridone, perinone, perylene, diketopyrrolopyrrole, indigo, thioindigo, dioxazine, triphenylmethane and quinophthalone compounds. For example, the organic pigments may be chosen from carmine lake, carbon black, aniline black, azo yellow, quinacridone, phthalocyanine blue, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, and the pigments obtained by oxidative polymerization of indole or phenolic derivatives as described in patent FR 2 679 771.

Nacres may be chosen from white pearlescent pigments such as mica coated with titanium or with bismuth oxychloride, colored pearlescent pigments such as titanium mica with iron oxides, titanium mica with in particular ferric blue or the chromium oxide, titanium mica with an organic pigment of the abovementioned type, and pearlescent pigments based on bismuth oxychloride.

The one or more colorants may optionally be included in the composition in an amount up to about 5%, such as up to about 4.5%, up to about 4%, up to about 3.5%, up to about 3%, up to about 2.5%, up to about 2%, up to about 1.5%, up to about 1%, up to about 0.75%, up to about 0.5%, up to about 0.25%, up to about 0.2%, or up to about 0.1%, weight, relative to the weight of the composition.

It should be understood that the greater amount of colorant added, the greater the effects of the film on the skin to hide skin imperfections, such as pores, pimples, dark spots, and the like. Therefore, the skilled artisan will be able to choose an amount of colorant appropriate for the composition, keeping in mind the intended use of the final formulation.

Film

When the compositions according to the disclosure are applied to the skin, the at least one thermoplastic elastomer, the at least one adhesive polymer, and the at least one filler together form a matrix that creates a film on the skin. The films formed by the compositions described herein form quickly, are long-lasting and durable, and have optical properties that are advantageous for a skin-tightening film, such as transparency, matte effect, and a soft focus effect which helps to blur skin imperfections so that they are less noticeable.

Additionally, as discussed above, the compositions according to the disclosure form a film that is stiffer than, and thus capable of tightening, human skin. Human skin has a Young Modulus in the range of 10 kPa to 100 kPa; thus, a film for tightening the skin should have a Young Modulus of greater than 100 kPa. The films that are formed by the compositions have Young Modulus' greater than 500 kPa (0.5 MPa) in some embodiments, greater than 1000 kPa (1 MPa) in some embodiments, greater than 5000 kPa (5 MPa) in some embodiments, and even greater than 10,000 kPa (10 MPa) in some embodiments. Additionally, the compositions according to the disclosure have sufficient consistency G* and phase angle below 45°, in order to form an effective and lasting film on the skin.

As such, the amounts and components of the composition should be chosen to provide a film on the skin that is capable of tightening the skin, while also blurring skin imperfections.

In various exemplary embodiments, for the best film properties, it may be advantageous for the total amount of thermoplastic elastomer plus adhesive polymer plus filler to be greater than about 10%, such as greater than about 15% or greater than about 20%, by weight, of the total weight of the composition.

In yet further exemplary embodiments, for the best film properties, it may be advantageous for amounts of the thermoplastic elastomer and adhesive polymer to be chosen so that the ratio of thermoplastic elastomer:adhesive polymer is in the range of about 1:10 to 10:1, in the range of about 1:5 to 5:1, or in the range of about 1:1 to 8:1.

The films may be formed quickly, for example within less than about 30 minutes, less than about 20 minutes, less than about 10 minutes, or less than about 5 minutes, after the composition is applied to the skin.

Films according to the disclosure may be long-lasting. For example, once the composition is applied to the skin and a film is formed, the film may remain substantially intact on the skin for a period of at least about 12 hours, such as at least about 24 hours, at least about 48 hours, or at least about 72 hours.

The films may also be durable. For example, the film may not rub off, may not come off with sweat, or when the film is contacted by water, makeup, lotions, or other products that the user may wish to put on the skin.

Methods

Methods of improving the appearance of the skin are also disclosed, said methods comprising applying a composition according to the disclosure onto the skin in order to form a film on the skin. Methods comprise tightening the skin, e.g. to get rid of wrinkles, eye bags, etc., and/or blurring or hiding skin imperfections, e.g. to camouflage pimples, pores, dark spots, etc.

According to various embodiments, different compositions may be applied to the skin to form films having different properties, such as compositions comprising greater or lesser amounts of pigments depending on whether skin imperfections may require more or less camouflage, etc.

It to be understood that, as used herein the terms "the," "a," or "an," mean "at least one," and should not be limited to "only one" unless explicitly indicated to the contrary. Thus, for example, reference to "a portion" includes examples having two or more such portions unless the context clearly indicates otherwise.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method that comprises A+B+C include embodiments where a method consists of A+B+C and embodiments where a method consists essentially of A+B+C. As described, the phrase "at least one of A, B, and C" is intended to include "at least one A or at least one B or at least one C," and is also intended to include "at least one A and at least one B and at least one C."

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints.

It is understood that when an amount of a component is given, it is intended to signify the amount of the active material.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

The compositions and methods according to the present disclosure can comprise, consist of, or consist essentially of the elements and limitations described herein, as well as any additional or optional ingredients, components, or limitations described herein or otherwise known in the art.

It will be apparent to those skilled in the art that various modifications and variations can be made in the delivery system, composition and methods of the invention without departing from the spirit or scope of the invention. Thus, it is intended that the present invention cover the modifications and variations of this invention provided that they come within the scope of the appended claims and their equivalents.

EXAMPLES

The following Examples are provided for illustrative purposes only, and are not intended to be limiting.

In each of the following examples, the amounts of components given are in terms of active material (AM).

Dynamic Mechanical Analysis (DMA)

The determination of Young Modulus of the films for all Examples was as follows. The film was made by using a draw down bar at 8" to cast the solution on a Teflon plate and dried the film at 40° C. in an oven overnight. The DMA Q800FR from TA instruments was used to measure the stress-strain response of the dried film. The deformation was applied from 0% strain to 200% strain at a rate of 100% strain/min at 32° C. Then the Young Modulus of the film was determined from the slope of the stress-strain curve in the linear viscoelastic regime.

Scanning Electron Microscope (SEM) Measurement

The film sample for SEM was made by using the same method as for DMA measurement. Subsequently, the film was cut into a 5×5 mm piece and loaded onto a stage with a double sided carbon tape. The sample was scanned with a Hitachi TM-1000 Tabletop SEM.

Rheology Measurement

The rheology of sample solutions was measured by using Rheometer AR-G2 from TA instruments. The dynamic oscillation mode was used with the parallel plate of 20 mm diameter at a gap of 200 µm.

The strain sweep from 0.001% to 1000% at an oscillation frequency of 1 rad/s was applied to the sample at 32° C. The value of elastic modulus G' and viscous modulus G" at 10% strain were recorded for each measured sample. The complex modulus G*(consistency) and phase angle δ collected at 10% strain (in linear viscoelastic regime) were calculated from the elastic modulus G' and viscous modulus G" by the following equations:

$$G^* = \sqrt{G'^2 + G''^2}$$

$$\delta = \arctan\left(\frac{G''}{G'}\right)$$

Haze and Transparency-BYK Haze-Guard

The film was made by using a draw down bar at 8" to cast the solution on a transparent plastic film and dried on bench for 3 hours. The BYK Haze-Guard instrument was used to measure the transparency and the haze of the film.

Gloss—BYK Glossmeter

The film was made by using a draw down bar at 8" to cast the solution on a transparent plastic film and dried on bench for 3 hours. The BYK Glossmeter was used to measure the gloss and matteness of the film.

Film Permeability

The film was made by using a draw down bar at 8" to cast the solution on a Teflon plate and dried the film at 40° C. in an oven overnight. The film was peeled off and cut to 5×5 cm pieces. Each piece was used to cover the top of a scintillation vial filled with 2 mL water, and a piece of Parafilm was used to wrap the piece of film on the side. The weight of each vial was measured immediately as well as different time points. The water weight loss of different films was plotted to the different time points and the evaporation was calculated by fitting the evaporation curve with a linear function. The water vapor permeability of the film (P) is calculated with the followed equation, where (J) is the water vapor permeation flux; (l) is the thickness of the film and the (Δp) is the water vapor pressure difference between the space sealed by the film in the vial and the outside of the film, which is the ambient:

$$P = J/(\Delta p/l)$$

Contact Angle Measurement

The film was made by using a draw down bar at 8" to cast the solution on a glass slide and dried on bench overnight. The contact angle of the film on the glass slide was measured by the Biolin Scientific Attension Tensiometer.

Speed of Drying

The film was made by using a draw down bar at 8" to cast the solution on a transparent plastic film and weighed regularly during a period of one hour.

Internal Constraint

The film was made by using a draw down bar at 8" to cast the solution on a nitrile band and let dry for a period of one hour. As the film shrinks upon drying, the surface of the nitrile band is measured by image analysis.

Transparency, Homogenizing Power and Whitening Power—Colorimeter MINOLTA

The film was made by casting the solution on a transparent plastic film using a draw down bar (2 mil) and left to dry on the bench for 1 hour. The Minolta colorimeter was used to measure the L, a*, b* and Y of the film, and of a skin tone sheet reference and black and white reference, in order to calculate the transparency, homogenizing power, and whitening power of the films.

Wear and Coverage

The films were applied on the cheeks of 3 panelists with pimples and pores along nose/cheek area and left for 6 hours. Last was evaluated through before/after pictures. Shininess, pore hiding, imperfections coverage for times both before and after were evaluated.

Example 1

Association of Thermoplastic Elastomer, Adhesive Polymer, and Filler

A thermoplastic elastomer, Kraton (25%), was dispersed in isoparaffin oil with a mechanical stirrer and heated to 90° C. Stirring continued at 90° C. for 1-2 hours until all Kraton polymer was dissolved and the polymer solution became clear. The desired amounts of oil dispersion (49% in isododecane) and silica silylate were added into the Kraton/isoparaffin oil solution at the specified ratios in a plastic container, and the solution was mixed with a high speed mixer at 2500 rpm/min for 5 minutes. The final solution was kept at room temperature and sealed to avoid the evaporation of solvents.

The following Table 1 shows the comparison of the film formed from compositions prepared according to the disclosure (Ex. 1), and three comparative compositions (Ex. 1C-1; 1C-2; 1C-3).

TABLE 1

Demonstration of association of the thermoplastic elastomer, adhesive polymer and filler for superior performance

| | Ex. 1 | Ex. 1C-1 | Ex. 1C-2 | Ex. 1C-3 |
|---|---|---|---|---|
| Ratio-Kraton (AM):OD (AM) | 1:1 | 1:0 | 0:1 | 1:1 |
| HYDROGENATED STYRENE/BUTADIENE COPOLYMER | 12.1% | 24.2% | 0.0% | 12.1% |
| OIL DISPERSION | 12.1% | 0.0% | 24.2% | 12.1% |
| SILICA SILYLATE | 3.0% | 3.0% | 3.0% | 0.0% |
| ISODODECANE | 38.3% | 38.3% | 38.3% | 41.3% |
| C8-9 ISOPARAFFIN | 34.5% | 34.5% | 34.5% | 34.5% |
| Total | 100.0% | 100.0% | 100.0% | 100.0% |
| G*(10% strain) Pa | 1772.5 | 6493.8 | 36.8 | 58.9 |
| δ (10% strain) ° | 35.4 | 28.0 | 35.0 | 57.2 |
| Film Young Modulus (MPa) at 32° C. | 32.7 | 7.4 | 42.9 | 10.75 |
| Film % Max strain before cracking | >100% | >100% | >100% | >100% |
| CONCLUSION | GOOD | Film is too soft | Formula is too fluid = film is too thin | Formula is too fluid = film is too thin |

The formulations and films were evaluated as set out above. From the examples, the consistency G* of the sample should be greater than about 100 Pa (at 10% strain) and the phase angle below about 45° for best results, as the formula needs to be a gel to make good film properties. If the formula is too fluid, the film will be too thin and the performance not good. Therefore, Examples 1 and 1C-1 satisfy these conditions at which G*>100 Pa and phase angle <45°.

Example 1 has the best Young Modulus and the best consistency, to provide a film having the best properties for skin tightening, demonstrating superior performance of the association of thermoplastic elastomer, adhesive polymer, and filler.

Example 2

Ratio of Thermoplastic Elastomer:Adhesive Polymer

The procedure for preparing the compositions of Example 2 is the same as described above for Example 1. The following Table 2 shows the comparison of the formulations according to the disclosure, and films formed therefrom (Ex. 2a; 2b; 2c), and two comparative compositions (Ex. 2C-1; 2C-2).

TABLE 2

Selection of optimal minimum/maximum ratio of thermoplastic elastomer:adhesive polymer

|  | Ex. 2a | Ex. 2b | Ex. 2c | Ex. 2C-1 | Ex. 2C-2 |
|---|---|---|---|---|---|
| Ratio-Kraton (AM):OD (AM) | 5 | 1 | 0.25 | 1 | 0 |
| HYDROGENATED STYRENE/BUTADIENE COPOLYMER | 20.1% | 12.1% | 4.8% | 24.2% | 0.0% |
| OIL DISPERSION | 4.1% | 12.1% | 19.4% | 0.0% | 24.2% |
| SILICA SILYLATE | 3.0% | 3.0% | 3.0% | 3.0% | 3.0% |
| ISODODECANE | 38.3% | 38.3% | 38.3% | 38.3% | 38.3% |
| C8-9 ISOPARAFFIN | 34.5% | 34.5% | 34.5% | 34.5% | 34.5% |
| Total | 100.0% | 100.0% | 100.0% | 100.0% | 100.0% |
| G*(10% strain) Pa | 3389.3 | 1772 | 386.9 | 6494 | 3675 |
| δ (10% strain) ° | 34.8 | 35 | 31.5 | 28.0 | 35 |
| Young Modulus (Mpa) at 32° C. | 13.7 | 29.8 | 78.2 | 8.0 | 43.5 |
| CONCLUSION | Film Acceptable | Good film properties | Good film properties | Film too soft | Formula too fluid = Film too thin |

The formulations and films were evaluated as set out above. From the results, Ex. 2a, 2b, and 2c all have good consistency with G*>100 Pa and phase angle less than 45° as well as Young modulus >100 kPa. Ex. 2C-1 (without the oil dispersion) with low Young modulus was too soft, and Ex. 2C-2 (without Kraton polymer) with high Young Modulus was too thin. Therefore, the results showed that if content of elastomer (Kraton) is high, it can make a too soft film, while with a high content of adhesive polymer (oil dispersion), the formulation is too fluid. As a result, the film becomes too thin and the performance is not good on skin. This shows that the ratio of thermoplastic elastomer to adhesive polymer optimally ranges from 1:5 and 5:1.

Example 3

Evaluation of Different Adhesive Polymers

Example 3A

Evaluation of Different Adhesive Polymers With $T_g$>25°

The thermoplastic elastomer, Kraton (25%), was dispersed in isoparaffin oil with a mechanical stirrer and heated to 90° C. Stirring continued at 90° C. for 1-2 hours until all Kraton polymer was dissolved and the polymer solution became clear. The desired amounts of adhesive polymer and silica silylate were added into the Kraton/isoparaffin oil solution at the specified ratios in a plastic container, and the solution was mixed with a high speed mixer at 2500 rpm/min for 5 minutes. The final solution was kept at room temperature and sealed to avoid the evaporation of solvents.

The following Table 3A shows the comparison of the film formed from compositions according to the disclosure (Ex. 3a; 3b; 3c).

TABLE 3A

Evaluation of different adhesive polymers with $T_g$ >25° C.

| | Ex. 3a | Ex. 3b | Ex. 3c |
|---|---|---|---|
| HYDROGENATED STYRENE/BUTADIENE COPOLYMER | 11.1% | 11.1% | 11.1% |
| OIL DISPERSION | 11.1% | — | — |
| HYDROGENATED POLYCYCLOPENTADIENE | — | 11.1% | — |
| HYDROGENATED STYRENE/METHYL STYRENE/INDENE COPOLYMER | — | — | 11.1% |
| ISODODECANE (AND) DIMETHICONE CROSSPOLYMER | 4.5% | 4.5% | 4.5% |
| SILICA SILYLATE | 3.0% | 5% | 5% |
| C8-9 ISOPARAFFIN | 33.3% | 33.3% | 33.3% |
| ISODODECANE | 37.0% | 37.0% | 37.0% |
| Total | 100.0% | 100.0% | 100.0% |
| Young Modulus (32 C., MPa) | 17.84 | 7.66 | 8.0 |
| CONCLUSION | Good mechanical properties | Good mechanical properties | Good mechanical properties |

The films were evaluated as set out above. The results in Table 3A show that Examples 3a-3c, prepared according to the disclosure with different adhesive polymers having a $T_g$ greater than 25° C., each provide films with good mechanical properties.

Example 3B

Evaluation of Polyacid Polymer as Adhesive Polymer

The procedure for preparing the compositions of Example 3B is the same as described above for Example 1. The following Table 3B shows the comparison of the formulations according to the disclosure with a polyacid, and films formed therefrom (Ex. 3d; 3e; 3f), with a comparative composition not comprising a polyacid (Ex. 3C-1).

TABLE 3B

Evaluation of polyacid polymer as adhesive polymer

|  | Ex. 3d | Ex. 3e | Ex. 3f | Ex 3C-1 |
|---|---|---|---|---|
| Ratio-thermoplastic elastomer (AM):polyacid (AM) | 2:1 | 4:1 | 8:1 | N/A |
| HYDROGENATED STYRENE/BUTADIENE COPOLYMER | 11.0% | 11.0% | 11.0% | 11.0% |
| C28-52 OLEFIN/UNDECYLENIC ACID COPOLYMER (Polyacid) | 5.5% | 2.8% | 1.4% | — |
| SILICA SILYLATE | 3.0% | 3.0% | 3.0% | 3.0% |
| C8-9 ISOPARAFFIN | 33.0% | 33.0% | 33.0% | 33.0% |
| ISODODECANE | 47.5% | 50.3% | 51.6% | 53.0% |
| Total | 100.0% | 100.0% | 100.0% | 100.0% |
| Young Modulus (MPa) at RT | 38.2 | 29.9 | 20.9 | 11.5 |
| CONCLUSION | Good | Good | Good | Too soft |

The films were evaluated as described above. The results in Table 3B demonstrate the effectiveness of a hyperbranched polyacid as the adhesive polymer over varying ratios.

Example 4

Efficacy of Films for Hiding Skin Imperfections

Example 4A

Composition

The procedure for preparing the composition of Example 4A is the same as described above for Example 1. The following Table 4A shows a composition prepared according to the disclosure (Ex. 4a) for forming a film on the skin.

TABLE 4A

Composition for forming a film

|  | Ex. 4a |
|---|---|
| HYDROGENATED STYRENE/BUTADIENE COPOLYMER | 12.1% |
| OIL DISPERSION | 12.1% |
| SILICA SILYLATE | 3.0% |
| ISODODECANE | 38.3% |
| C8-9 ISOPARAFFIN | 34.5% |
| Total | 100.0% |
| Transparency | 90.5% |
| Haze | 91.4% |

The film was evaluated as set out above. The high transparency and haze achieved by the film prepared according to the disclosure demonstrates the effectiveness of the films to blur or hide skin imperfections.

Example 4B

Efficacy of Film Formed

The film prepared according to Example 4A was applied to the skin of the eye area of 6 test subjects with grade 4 eye wrinkles and eye bags, and 6 test subjects with grade 4 crow's feet. The film was allowed to dry for 10 minutes, after which the improvements in the appearance of the eye wrinkles and crow's feet were evaluated periodically. The results are shown in Table 4B.

TABLE 4B

Efficacy of film at improving appearance of skin

|  | 10 min | 30 min | 3 hr | 6 hr |
|---|---|---|---|---|
| Under eye bags | −2 grade | −2.4 grade | −2.5 grade | −2.3 grade |
| Crow's feet | −2 grade | −2.5 grade | −2.4 grade | −2 grade |
| Under eye wrinkles | −2.5 grade | −2.5 grade | −2.5 grade | −2 grade |

Clinical Evaluation was based on a Eye wrinkles and Eye bags grading atlas (Skin Aging Atlas, vol 1, Caucasian type, Roland Bazin, Eric Doublet, Editions Med'Com, 2007). The results in Table 4B demonstrate that the film prepared according to the disclosure significantly improves the appearance of eye bags, eye wrinkles, and crow's feet. The results also demonstrate that over time, the improvement stays approximately constant, showing that the film provides long-lasting results.

Example 5

Addition of Humectant for Improving Moisture

The thermoplastic elastomer, Kraton (25%), was dispersed in isoparaffin oil with a mechanical stirrer and heated to 90° C. Stirring continued at 90° C. for 1-2 hours until all Kraton polymer was dissolved and the polymer solution became clear. The desired amounts of adhesive polymer and silica silylate were added into the Kraton/isoparaffin oil solution at the specified ratios in a plastic container, and the solution was mixed with a high speed mixer at 2500 rpm/min for 5 minutes, then glycerin was added and mixing continued. The final solution was kept at room temperature and sealed to avoid the evaporation of solvents.

The following Table 5 shows the evaluation of the film formed from a composition according to the disclosure with glycerin (Ex. 5) compared to a comparative film formed from a composition according to the disclosure but not containing glycerin (Ex. 5C-1).

TABLE 5

Capacity of the composition to include glycerin as moisturizing agent without affecting the performance of the film

|  | Ex. 5 | Ex. 5C-1 |
|---|---|---|
| HYDROGENATED STYRENE/BUTADIENE COPOLYMER | 11.3% | 11.3% |
| OIL DISPERSION | 11.3% | 11.3% |
| SILICA SILYLATE | 3.0% | 3.0% |
| Glycerin | 5.0% | — |

TABLE 5-continued

Capacity of the composition to include glycerin as moisturizing agent without affecting the performance of the film

| | Ex. 5 | Ex. 5C-1 |
|---|---|---|
| ISODODECANE | 37.5% | 42.5% |
| C8-9 ISOPARAFFIN | 32.0% | 32.0% |
| Total | 100.0% | 100.0% |
| Young Modulus (Mpa) at 32° C. | 34.3 | 34.0 |
| Mechanical properties | Good | Good |
| Film Aspect | Transparent, soft focus | Transparent, soft focus |
| Feel on skin | Moisturizing | Not moisturizing |

The films were evaluated as described above. The results in Table 5 demonstrate that the film formed from a composition according to the disclosure and containing a humectant (glycerin) surprisingly did not negatively affect the mechanical or optical properties of the film, yet provided a moisturizing sensation to the film on the skin compared to a film not containing the humectant.

Example 6

Addition of Water

The thermoplastic elastomer, Kraton (25%), was dispersed in isoparaffin oil with a mechanical stirrer and heated to 90° C. Stirring continued at 90° C. for 1-2 hours until all Kraton polymer was dissolved and the polymer solution became clear. The desired amounts of adhesive polymer and silica silylate were added into the Kraton/isoparaffin oil solution at the specified ratios in a plastic container, and the solution was mixed with a high speed mixer at 2500 rpm/min for 5 minutes, then the glycerin and/or water were added and mixing continued. The final solution was kept at room temperature and sealed to avoid the evaporation of solvents.

The following Table 6 shows the evaluation of the films formed from a composition according to the disclosure with glycerin (Ex. 6a), or with glycerin and water (Ex. 6b-6e).

The films were evaluated as described above. The results in Table 6 demonstrate that, surprisingly, the addition of water into the composition improves the mechanical properties, enhancing cohesion as seen by the SEM results. Additionally, the optical properties, such as transparency and soft focus, were unaffected.

Example 7

Addition of Silicone Elastomer

The thermoplastic elastomer, Kraton (25%), was dispersed in isoparaffin oil with a mechanical stirrer and heated to 90° C. Stirring continued at 90° C. for 1-2 hours until all Kraton polymer was dissolved and the polymer solution became clear. The desired amounts of oil dispersion (49% in isododecane), silica silylate, and silicone elastomer (DC EL-8040 ID silicone organic blend at 18% isododecane) were added into the Kraton/isoparaffin oil solution at the specified ratios in a plastic container, and the solution was mixed with a high speed mixer at 2500 rpm/min for 5 minutes. The final solution was kept at room temperature and sealed to avoid the evaporation of solvents.

The film was plated on contrast cards with an 8 mL draw-down bar. After drying overnight, the film was peeled off for DMA measurements or just kept on the substrate for optical effects.

The following Table 7 shows the evaluation of the film formed from a composition according to the disclosure with a silicone elastomer (Ex. 7) compared to a comparative film formed from a composition according to the disclosure but not containing a silicone elastomer (Ex. 7C-1).

TABLE 7

Additional benefits brought by silicone elastomer

| | Ex. 7 | Ex. 7C-1 |
|---|---|---|
| HYDROGENATED STYRENE/BUTADIENE COPOLYMER | 11.1% | 11.1% |

TABLE 6

Capacity of the composition to include water

| | Ex. 6a | Ex. 6b | Ex. 6c | Ex. 6d | Ex. 6e |
|---|---|---|---|---|---|
| HYDROGENATED STYRENE/BUTADIENE COPOLYMER | 10.8% | 10.8% | 10.8% | 10.8% | 10.8% |
| OIL DISPERSION | 10.8% | 10.8% | 10.8% | 10.8% | 10.8% |
| C8-9 isoparrafin | 32.4% | 32.4% | 32.4% | 32.4% | 32.4% |
| Isododecane | 24.7% | 23.7% | 22.7% | 20.7% | 14.7% |
| SILICA SILYLATE | 2.7% | 2.7% | 2.7% | 2.7% | 2.7% |
| SYNTHETIC WAX | 1.8% | 1.8% | 1.8% | 1.8% | 1.8% |
| Glycerin | 14.2% | 14.2% | 14.2% | 14.2% | 14.2% |
| CETYL PEG/PPG-10/1 DIMETHICONE | 2.0% | 2.0% | 2.0% | 2.0% | 2.0% |
| POLYGLYCERYL-4 ISOSTEARATE | 0.6% | 0.6% | 0.6% | 0.6% | 0.6% |
| water | — | 1.0% | 2.0% | 4.0% | 10.0% |
| Total | 100.0% | 100.0% | 100.0% | 100.0% | 100.0% |
| Young Modulus (MPa) at 25° C. | 21.6 | 30.3 | 33.9 | 34.7 | 42.4 |
| SEM measurement Pore density (qualitative) | high | medium | low | low | low |
| Aspect | translucent | translucent | translucent | translucent | slightly white |
| CONCLUSION | GOOD film properties | GOOD film properties | GOOD film properties | GOOD film properties | ACCEPTABLE film properties |

TABLE 7-continued

Additional benefits brought by silicone elastomer

|  | Ex. 7 | Ex. 7C-1 |
|---|---|---|
| OIL DISPERSION | 11.1% | 11.1% |
| SILICA SILYLATE | 3.0% | 3.0% |
| C8-9 ISOPARAFFIN | 33.3% | 33.3% |
| ISODODECANE | 37.0% | 41.5% |
| DIMETHICONE CROSSPOLYMER | 4.5% | — |
| Total | 100.0% | 100.0% |
| Transparency % | 91.3 | 90.5 |
| Haze % | 97.7 | 91.4 |
| Permeability to water (mg/h/cm2 · µm) | 26 | 14 |
| Contact angle with water | 121 | 112 |
| Contact angle with water (°) | 70 | 0 |
| Young modulus (Storage modulus, 32 C., Mpa) | 24.7 | 33.5 |
| Friction coefficient (1 pass) | 0.26 | 0.99 |

The films were evaluated as described above. The results in Table 7 demonstrate that the addition of a silicone elastomer improves the optical properties of the film, improving soft focus effects without negatively affecting transparency. Additionally, the water-permeability of the film is improved, with is advantageous as sweat can pass through the film which allows the tightening properties to remain over a long period of time.

Example 8

Evaluation of Different Silicone Elastomers

The procedure for preparing the compositions of Example 8 is the same as described above for Example 7. The following Table 8 shows the evaluation of films formed with different silicone elastomers (Ex. 8a, 8b, 8c, 8d).

TABLE 8

Selection of silicone elastomer for best performance

|  | Ex. 8a | Ex. 8b | Ex. 8c | Ex. 8d |
|---|---|---|---|---|
| HYDROGENATED STYRENE/BUTADIENE COPOLYMER | 11.1% | 11.1% | 11.1% | 11.1% |
| OIL DISPERSION | 11.1% | 11.1% | 11.1% | 11.1% |
| SILICA SILYLATE | 3.0% | 3.0% | 3.0% | 3.0% |
| C8-9 ISOPARAFFIN | 33.3% | 33.3% | 33.3% | 33.3% |
| ISODODECANE | 37.0% | 37.0% | 37.0% | 37.0% |
| ISODODECANE (AND) DIMETHICONE CROSSPOLYMER (18% AM) | 4.5% | — | — | — |
| DIMETHICONE/BIS-ISOBUTYL PPG-20 CROSSPOLYMER (17% AM in isododecane) | — | 4.5% | — | — |
| PEG-15/LAURYL DIMETHICONE CROSSPOLYMER (25% AM in isododecane) | — | — | 4.5% | — |
| ISODODECANE (and) VINYLDIMETHYL/TRIMETHYLSILOXYSILICATE STEARYL DIMETHICONE CROSSPOLYMER (20% AM in isododecane) | — | — | — | 4.5% |
| Total | 100.0% | 100.0% | 100.0% | 100.0% |
| Contact Angle (°) - water | 120.8 | 114.8 | 112.8 | 123.5 |
| Contact Angle (°) - sebum | 70.2 | Close to 0 | Close to 0 | 91.4 |

The films were evaluated as described above. The results in Table 8, showing high contact angle with water, demonstrate that the films containing different silicone elastomers show good resistance to water.

Example 9

Evaluation of Different Fillers

The procedure for preparing the compositions of Example 9 is the same as described above for Example 7. The following Table 9 shows the evaluation of films formed according to the disclosure with different silica particles (Ex. 9a, 9b), compared with comparative films (Ex. 9C-1, 9C-2, 9C-3).

TABLE 9

Selection of the filler

|  | Ex. 9a | Ex. 9b | Ex 9C-1 | Ex. 9C-2 | Ex. 9C-3 |
|---|---|---|---|---|---|
| HYDROGENATED STYRENE/BUTADIENE COPOLYMER | 11.1% | 11.1% | 11.1% | 11.1% | 11.1% |

TABLE 9-continued

| Selection of the filler | | | | | |
|---|---|---|---|---|---|
| | Ex. 9a | Ex. 9b | Ex 9C-1 | Ex. 9C-2 | Ex. 9C-3 |
| OIL DISPERSION (49% AM) | 11.1% | 11.1% | 11.1% | 11.1% | 11.1% |
| SILICA SILYLATE: DOW CORNING VM-2270 AEROGEL FINE PARTICLES (size: 8 um Surf. Area: 600-800 m2/g) | 3.0% | — | — | — | — |
| SILICA DIMETHYL SILYLATE: WACKER HDK H 15 (size: 16 nm Surf. Area: 90-130 m2/g) | — | — | 3.0% | — | — |
| SILICA SILYLATE: CAB-O-SIL TS-530 (size: 200-300 nm Surf. Area: 205-245 m2/g) | — | 3.0% | — | — | — |
| STYRENE/ACRYLATES COPOLYMER: Sunspheres Rhom & Haas (size: 300-350 nm Surf. Area: N/A) | — | — | — | 3.0% | — |
| POLYMETHYL METHACRYLATE: SEPIMAT H 10 Seppic (size: 5-20 um Surf. Area: 2.1-2.3 m2/g) | — | — | — | — | 3.0% |
| C8-9 ISOPARAFFIN | 33.3% | 33.3% | 33.3% | 33.3% | 33.3% |
| ISODODECANE | 37.0% | 37.0% | 37.0% | 37.0% | 37.0% |
| ISODODECANE (AND) DIMETHICONE CROSSPOLYMER (18% AM) | 4.5% | 4.5% | 4.5% | 4.5% | 4.5% |
| Total | 100.0% | 100.0% | 100.0% | 100.0% | 100.0% |
| Film homogeneity | good | good | good | good | good |
| Young Modulus (32° C., MPa) | 24.7 | 20.8 | 15.2 | 2.7 | 8.1 |
| Transparency % | 91.3 | 90.4 | 90.6 | 82.5 | 90.1 |
| Haze % | 97.7 | 86.9 | 93.3 | 79.8 | 89.2 |
| Gloss | 9.1 | 8.6 | 9.3 | 10.6 | 10.3 |
| CONCLUSION | GOOD - Best haze | GOOD | GOOD | GOOD film but too soft; lowest soft focus | POOR |

The films were evaluated as described above. The results in Table 9 demonstrate that the addition of different silica particles provide improved mechanical properties of the film, as shown by the Young Modulus measurements. The improvement is even more pronounced with silicas with particle sizes greater than 100 nm and with higher specific surface area. Optical properties, including soft focus, and sebum absorption are also improved.

Example 10

Comparison of Different Filler Ratios

The procedure for preparing the compositions of Example 10 is the same as described above for Example 7. The following Table 10 shows the evaluation of films formed with different amounts of silica particles (Ex. 10a, 10b, 10c, 10d).

TABLE 10

| Selection of optimal ratio of filler in the composition | | | | |
|---|---|---|---|---|
| | Ex. 10a | Ex. 10b | Ex. 10c | Ex. 10d |
| HYDROGENATED STYRENE/BUTADIENE COPOLYMER | 11.1% | 11.1% | 11.1% | 11.1% |
| OIL DISPERSION (49% AM) | 11.1% | 11.1% | 11.1% | 11.1% |
| SILICA SILYLATE (Aerogel) | 0.5% | 1.5% | 3.0% | 4.0% |
| C8-9 ISOPARAFFIN | 33.3% | 33.3% | 33.3% | 33.3% |
| ISODODECANE | 39.5% | 38.5% | 37.0% | 36.0% |

TABLE 10-continued

Selection of optimal ratio of filler in the composition

|  | Ex. 10a | Ex. 10b | Ex. 10c | Ex. 10d |
|---|---|---|---|---|
| ISODODECANE (AND) DIMETHICONE CROSSPOLYMER (18% AM) | 4.5% | 4.5% | 4.5% | 4.5% |
| Total | 100.0% | 100.0% | 100.0% | 100.0% |
| Young Modulus (32° C., MPa) | 9.5 | 13.4 | 30.2 | 40.4 |
| Film aspect | Transparent soft focus | Transparent soft focus | Transparent soft focus | Transparent soft focus - A bit white |
| Film aspect on skin | OK - tend to mark wrinkle | Good | Good | OK - tend to create artificial wrinkles |

The films were evaluated as described above. The results in Table 10 demonstrate that different amounts of Aerogel particles provide satisfactory results.

Example 11

Evaluation of Solvents

The procedure for preparing the compositions of Example 11 is the same as described above for Example 7. The following Table 11 shows the evaluation of a film formed according to the disclosure having a solvent with vapor pressure over 1000 Pa at room temperature (Ex. 11) compared to a comparative film not having a solvent with vapor pressure over 1000 Pa at room temperature (Ex. 11C-1).

TABLE 11

Selection of solvent for optimal performance

|  | Ex. 11 | Ex. 11C-1 |
|---|---|---|
| HYDROGENATED STYRENE/BUTADIENE COPOLYMER | 11.10% | 11.10% |
| OIL DISPERSION | 11.10% | 11.10% |
| SILICA SILYLATE | 3.00% | 3.00% |
| C8-9 ISOPARAFFIN | 33.30% | — |
| ISODODECANE | 37.00% | 70.30% |
| ISODODECANE (AND) DIMETHICONE CROSSPOLYMER | 4.50% | 4.50% |
| Total | 100.0% | 100.0% |
| INTERNAL CONSTRAINT (1-4; 1 lowest/4 highest) | 4 | 2 |
| SPEED OF DRYING | 7 min | 30 min |
| YOUNG MODULUS (32 C.) at 1 hr | 24.7 | 18.5 |
| TIGHTENING FEEL (skin) | STRONG | AVERAGE |

The films were evaluated as described above. The tightening effect of the film was evaluated after application to the skin of 5 panelists under the eye area, who rated the tightening sensation as strong, average, or low.

The results in Table 11 demonstrate that use of a solvent with vapor pressure over 1000 Pa at room temperature shows better results. As also seen, a solvent with vapor pressure lower than 25 Pa at room temperature has poorer results, although some tightening was noted.

Example 12

Addition of Pigments

The thermoplastic elastomer, Kraton (25%), was dispersed in isoparaffin oil with a mechanical stirrer and heated to 90° C. Stirring continued at 90° C. for 1-2 hours until all Kraton polymer was dissolved and the polymer solution became clear. The desired amounts of oil dispersion (49% in isododecane), silica silylate, silicone elastomer (DC EL-8040 ID silicone organic blend at 18% isododecane), and pigments were added into the Kraton/isoparaffin oil solution at the specified ratios in a plastic container, and the solution was mixed with a high speed mixer at 2500 rpm/min for 5 minutes. The final solution was kept at room temperature and sealed to avoid the evaporation of solvents.

The following Table 12 shows the comparison of the formulations according to the disclosure with pigments, and films formed therefrom (Ex. 12a; 12b; 12c), and two comparative commercial formulations.

TABLE 12

Additional benefits due to addition of pigments

|  | Ex. 12a | Ex. 12b | Ex. 12c | Teint Idole Lancome | Revitalift Miracle Blur (L'Oreal Paris) |
|---|---|---|---|---|---|
| HYDROGENATED STYRENE/BUTADIENE COPOLYMER | 11.100% | 11.100% | 11.100% |  |  |
| OIL DISPERSION | 11.074% | 11.074% | 11.074% |  |  |
| SILICA SILYLATE | 3% | 3% | 3% |  |  |
| ISODODECANE | 37% | 36.875% | 35.525% |  |  |
| C8-9 ISOPARAFFIN | 33.300% | 33.300% | 33.300% |  |  |

TABLE 12-continued

Additional benefits due to addition of pigments

| | Ex. 12a | Ex. 12b | Ex. 12c | Teint Idole Lancome | Revitalift Miracle Blur (L'Oreal Paris) |
|---|---|---|---|---|---|
| SILICONE ELASTOMER | 4.500% | 4.500% | 4.500% | | |
| TITANIUM DIOXIDE | — | 0.109% | 1.085% | | |
| IRON OXIDE, RED | — | 0.003% | 0.026% | | |
| IRON OXIDE, BLACK | — | 0.001% | 0.007% | | |
| IRON OXIDE, YELLOW | — | 0.008% | 0.083% | | |
| NYLON-12 | — | 0.030% | 0.30% | | |
| Total | 100.000% | 100.000% | 100.000% | | |
| Transparency | 84.6 | 79.01 | 43.00 | 13.59 | 86.03 |
| Haze | 96.7 | 96.4 | 103 | 103 | 74.4 |
| Homogenizing power | 35.03 | 40.95 | 118.25 | 460.34 | 31.12 |
| Whitening power | 15.18 | 20.98 | 35.10 | 28.91 | 13.93 |
| Efficacy/lastingness on pores | +++/+++ | | | | ++/+ |
| Efficacy/lastingness on pimple hiding | | | +++/+++ | ++/++ | |

The films were evaluated as described above. Ex. 12a, with no pigment, shows the effect of high soft focus and high matte effect to blur pores. The film is long-lasting. Ex. 12b, with pigments, shows that the haze and whitening power are increased, and Ex. 12c, with ten times more pigments, shows even greater haze and whitening for a greater soft focus effect, demonstrating a strong ability to hide more prominent skin imperfections, such as pimples. Both the Ex. 12b and Ex. 12c films are long-lasting. All of Ex. 12a, 12b, and 12c show better results in hiding or blurring skin imperfections, while being longer-lasting, than either of the comparative commercial formulations.

The results in Table 12 demonstrate that with no pigment, the films have a soft focus effect and are long lasting with an ability to blur skin imperfections, and with pigment, the films have a strong ability to hide skin imperfections while remaining long-lasting.

We claim:

1. A skin tightening composition comprising:
    a. at least one thermoplastic elastomer;
    b. at least one adhesive polymer chosen from polymer particles of $C_1$-$C_4$ alkyl(methacrylate)polymer stabilized in a non-aqueous dispersion, or hyperbranched polyacids;
    c. at least one filler, and
    d. at least one silicone elastomer comprising at least one silicone crosspolymer dispersed in oil, wherein the at least one silicone crosspolymer dispersed in oil comprises vinyldimethyl/trimethylsiloxysilicate stearyl dimethicone crosspolymer in isododecane, wherein the at least one silicone elastomer is present in an amount ranging from 1% to 10% by weight, relative to the weight of the composition,
    wherein the at least one thermoplastic elastomer has at least two glass transition temperatures ($T_g$) and comprises one or more hard segment attached to one or more soft segment,
    wherein the weight ratio of the at least one thermoplastic elastomer to the at least one adhesive polymer is in the range of 1:1 to 5:1.

2. The skin tightening composition of claim 1, wherein the at least one thermoplastic elastomer has a first $T_g$ below about 0° C., and a second $T_g$ greater than about 25° C.

3. The skin tightening composition of claim 1, wherein the at least one thermoplastic elastomer is chosen from diblock, triblock, multiblock, radial, and/or star copolymers.

4. The skin tightening composition of claim 1, wherein the at least one thermoplastic elastomer has a first $T_g$ greater than about 40° C., and a second $T_g$ less than about −50° C.

5. The skin tightening composition of claim 1, wherein the at least one thermoplastic elastomer is chosen from semicrystalline block copolymers.

6. The skin tightening composition of claim 5, wherein the semicrystalline block copolymers comprise at least one moiety corresponding to formula (I) and/or at least one moiety corresponding to formula (II):

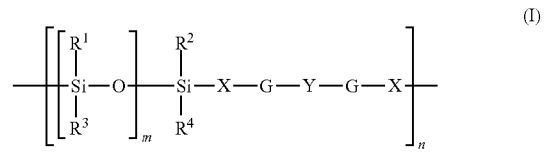

wherein:
1) $R^1$, $R^2$, $R^3$ and $R^4$, which may be identical or different, represent a group chosen from: (a) linear, branched or cyclic, saturated or unsaturated, $C_1$ to $C_{40}$ hydrocarbon-based groups, optionally containing in their chain one or more oxygen, sulphur and/or nitrogen atoms, and optionally being partially or totally substituted with fluorine atoms, (b) $C_6$ to $C_{10}$ aryl groups, optionally substituted with one or more $C_1$ to $C_4$ alkyl groups, and/or (c) polyorganosiloxane chains optionally containing one or more oxygen, sulphur and/or nitrogen atoms;
2) X, which may be identical or different, represents a linear or branched $C_1$ to $C_{30}$ alkylenediyl group, optionally containing in its chain one or more oxygen and/or nitrogen atoms;
3) Y is a saturated or unsaturated, $C_1$ to $C_{50}$ linear or branched divalent alkylene, arylene, cycloalkylene, alkylarylene or arylalkylene group, optionally comprising one or more oxygen, sulphur and/or nitrogen atoms, and/or optionally substituted with one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with one to three $C_1$ to $C_3$ alkyl, $C_1$ to $C_3$ hydroxyalkyl, and/or $C_1$ to $C_6$ aminoalkyl groups;

4) G, which may be identical or different, represents a group chosen from ester, amide, sulphonamide, carbamate, thiocarbamate, urea, thiourea groups, and/or combinations thereof;

5) m is an integer ranging from 1 to 1,000; and 6) n is an integer ranging from 2 to 500;

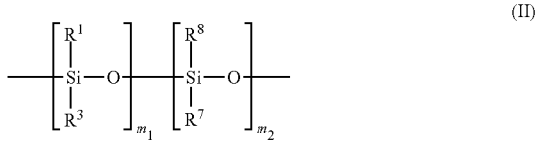

wherein:
$R^1$ and R, which may be identical or different, are as defined above for formula (I), $R^7$ represents a group as defined above for $R^1$ and $R^3$, or represents a group of formula —X-G-$R^9$ in which X and G are as defined above for formula (I) and $R^9$ represents a hydrogen atom or a linear, branched or cyclic, saturated or unsaturated, $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups, $R^8$ represents a group of formula —X-G-$R^9$ in which X, G and $R^9$ are as defined above, $m_1$ is an integer ranging from 1 to 998, and $m_2$ is an integer ranging from 2 to 500.

7. The skin tightening composition of claim 5, wherein the semicrystalline block copolymers comprise at least one moiety corresponding to formula (III) and/or at least one moiety corresponding to formula (IV):

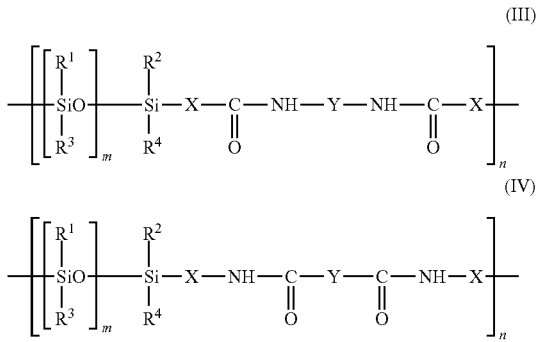

wherein:
(a) $R^1$, $R^2$, $R^3$, and $R^4$ are the same or different and may be selected from the group consisting of methyl, ethyl, propyl, isopropyl, a siloxane chain, and phenyl;
(b) X is a linear or branched chain alkylene having 1-30 carbons;
(c) Y is selected from the group consisting of linear or branched chain alkylenes having 1-40 carbons;
(d) m is a number between 1 and 700; and
(e) n is a number between 1 and 500.

8. The skin tightening composition of claim 1, wherein the at least one thermoplastic elastomer is present in the composition in an amount ranging from about 5% to about 25% by weight, relative to the total weight of the composition.

9. The skin tightening composition of claim 1, wherein the at least one adhesive polymer chosen from polymer particles of $C_1$-$C_4$ alkyl(methacrylate)polymer stabilized in a non-aqueous dispersion, or hyperbranched polyacids has a $T_g$ greater than about 25° C.

10. The skin tightening composition of claim 1, wherein the at least one adhesive polymer chosen from polymer particles of $C_1$-$C_4$ alkyl(methacrylate)polymer stabilized in a non-aqueous dispersion, or hyperbranched polyacids has a $T_g$ less than about 25° C.

11. The skin tightening composition of claim 1, wherein the at least one adhesive polymer is chosen from hyperbranched polyacids comprising at least two carboxyl groups.

12. The skin tightening composition of claim 11, wherein the hyperbranched polyacids have a molecular weight (Mw) ranging from about 500 to about 25,000, a viscosity at 210° F. ranging from 0.01 Pas to 10 Pas, and/or an acid number ranging from about 20 to about 400 mg/KOH.

13. The skin tightening composition of claim 11, wherein the hyperbranched polyacids are chosen from $C_{30+}$ olefin/ undecylenic acid copolymers.

14. The skin tightening composition of claim 1, wherein the at least one adhesive polymer chosen from polymer particles of $C_1$-$C_4$ alkyl(methacrylate)polymer stabilized in a non-aqueous dispersion, or hyperbranched polyacids is chosen from acrylic type film formers.

15. The skin tightening composition of claim 1, wherein the at least one adhesive polymer chosen from polymer particles of $C_1$-$C_4$ alkyl(methacrylate)polymer stabilized in a non-aqueous dispersion, or hyperbranched polyacids is chosen from copolymers containing at least one apolar monomer, at least one olefinically unsaturated monomer, and at least one vinylically functionalized monomer.

16. The skin tightening composition of claim 1, wherein the at least one adhesive polymer is present in the composition in an amount ranging from about 5% to about 25% by weight, relative to the total weight of the composition.

17. The skin tightening composition of claim 1, wherein the at least one filler is chosen from fillers having a particle size greater than about 100 nm, and/or a specific surface area greater than about 200 $m^2$/g.

18. The skin tightening composition of claim 1, wherein the at least one filler is chosen from silica particles, hydrophobic silica aerogel particles, or aerogel particles of hydrophobic silica surface-modified with trimethylsilyl groups.

19. The skin tightening composition of claim 1, wherein the at least one filler is present in the composition in an amount ranging from about 0.1% to about 20% by weight, relative to the weight of the composition.

20. The skin tightening composition of claim 1, further comprising at least one additional component chosen from solvents, humectants, water, and/or colorants.

21. The skin tightening composition of claim 1, wherein the at least one thermoplastic elastomer, at least one adhesive polymer, and at least one filler are present in a combined amount of greater than about 10% by weight, relative to the weight of the composition.

22. A method for improving the appearance of the skin, said method comprising forming a film on the skin by applying a composition comprising:

a. at least one thermoplastic elastomer;
b. at least one adhesive polymer chosen from polymer particles of $C_1$-$C_4$ alkyl(methacrylate)polymer stabilized in a non-aqueous dispersion, or hyperbranched polyacids;
c. at least one filler, and
d. at least one silicone elastomer comprising at least one silicone crosspolymer dispersed in oil, wherein the at least one silicone crosspolymer dispersed in oil comprises vinyldimethyl/trimethylsiloxysilicate stearyl dimethicone crosspolymer in isododecane, wherein the at least one silicone elastomer is present in an amount ranging from 1% to 10% by weight, relative to the weight of the composition, wherein the at least one thermoplastic elastomer has at least two glass transition temperatures ($T_g$) and comprises one or more hard segment attached to one or more soft segment;

wherein the weight ratio of the at least one thermoplastic elastomer to the at least one adhesive polymer is in the range of 1:1 to 5:1; and wherein the Young Modulus of the film formed on the skin is greater than about 500 kPa.

* * * * *